United States Patent
Gotlib et al.

(10) Patent No.: US 8,620,678 B2
(45) Date of Patent: Dec. 31, 2013

(54) MEDICAL INFORMATION QUERY SYSTEM

(75) Inventors: Phyllis Gotlib, Tel Aviv (IL); Ido Schoenberg, Tel Aviv (IL); Roy Schoenberg, Tel Aviv (IL)

(73) Assignee: iMD Soft Ltd., Needham, MA (US)

( * ) Notice: Subject to any disclaimer, the term of this patent is extended or adjusted under 35 U.S.C. 154(b) by 1348 days.

(21) Appl. No.: 10/355,527

(22) Filed: Jan. 31, 2003

(65) Prior Publication Data
US 2004/0153343 A1 Aug. 5, 2004

(51) Int. Cl.
G06Q 10/00 (2006.01)
G06Q 50/00 (2012.01)

(52) U.S. Cl.
USPC .................................. 705/2; 705/3

(58) Field of Classification Search
USPC ........................................ 705/2–5
See application file for complete search history.

(56) References Cited

U.S. PATENT DOCUMENTS

| | | |
|---|---|---|
| 3,646,606 A | 2/1972 | Buxton et al. |
| 4,489,387 A | 12/1984 | Lamb et al. |
| 4,709,331 A | 11/1987 | Barkett et al. |
| 4,719,338 A | 1/1988 | Avery et al. |
| 4,731,725 A | 3/1988 | Suto et al. |
| 4,736,322 A | 4/1988 | Clifford |
| 4,807,170 A | 2/1989 | Kulli et al. |
| 4,835,372 A | 5/1989 | Gombrich et al. |
| 4,838,275 A | 6/1989 | Lee |
| 4,852,570 A | 8/1989 | Levine |
| 4,878,175 A | 10/1989 | Norden-Paul et al. |
| 5,065,315 A | 11/1991 | Garcia |
| 5,199,439 A | 4/1993 | Zimmerman et al. |
| 5,255,187 A | 10/1993 | Sorensen |
| 5,262,944 A | 11/1993 | Weisner et al. |
| 5,301,105 A | 4/1994 | Cummings, Jr. |
| 5,305,205 A | 4/1994 | Weber et al. |
| 5,307,263 A | 4/1994 | Brown |
| 5,321,800 A | 6/1994 | Lesser |
| 5,335,346 A | 8/1994 | Fabbio |
| 5,348,008 A | 9/1994 | Bornn et al. |
| 5,361,202 A | 11/1994 | Doue |
| 5,398,300 A | 3/1995 | Levey |
| 5,404,292 A | 4/1995 | Hendrickson |

(Continued)

FOREIGN PATENT DOCUMENTS

| | | |
|---|---|---|
| EP | 0505627 | 9/1992 |
| WO | WO 98/29790 | 7/1998 |

(Continued)

OTHER PUBLICATIONS

Andrews, Robert D. et al., "Computer Charting: An Evaluation of a Respiratory Care Computer System" *Respiratory Care*, vol. 30, No. 8, Aug. 1985; pp. 695-707.

(Continued)

*Primary Examiner* — Sheetal R Rangrej
(74) *Attorney, Agent, or Firm* — Fish & Richardson P.C.

(57) ABSTRACT

A query system is provided for retrieving information from a medical information system, or its databases. A user interactive query wizard facilitates creation of query scripts for retrieval of information from the medical information system. Queries may be performed across a set of patients, hospitals or clinical resources. Query results are presented via an output device, such as a computer display. These results may be exported to other applications, such as known office or desktop applications, or other systems, such as database systems.

32 Claims, 8 Drawing Sheets

(56) References Cited

U.S. PATENT DOCUMENTS

| | | |
|---|---|---|
| 5,417,717 A | 5/1995 | Salo et al. |
| 5,447,164 A | 9/1995 | Shaya et al. |
| 5,482,050 A | 1/1996 | Smokoff et al. |
| 5,544,649 A | 8/1996 | David et al. |
| 5,544,661 A | 8/1996 | Davis et al. |
| 5,572,422 A | 11/1996 | Nematbakhsh et al. |
| 5,574,828 A | 11/1996 | Hayward et al. |
| 5,576,952 A | 11/1996 | Stutman et al. |
| 5,592,945 A | 1/1997 | Fiedler |
| 5,594,638 A | 1/1997 | Iliff |
| 5,619,991 A | 4/1997 | Sloane |
| 5,630,664 A | 5/1997 | Farrelly |
| 5,640,953 A | 6/1997 | Bishop et al. |
| 5,678,562 A | 10/1997 | Sellers |
| 5,682,526 A | 10/1997 | Smokoff et al. |
| 5,687,717 A | 11/1997 | Halpern et al. |
| 5,701,894 A | 12/1997 | Cherry et al. |
| 5,704,350 A | 1/1998 | Williams, III |
| 5,713,350 A | 2/1998 | Yokota et al. |
| 5,715,451 A * | 2/1998 | Marlin ............... 707/104.1 |
| 5,722,999 A | 3/1998 | Snell |
| 5,724,580 A | 3/1998 | Levin et al. |
| 5,729,479 A | 3/1998 | Golan |
| 5,752,621 A | 5/1998 | Passamante |
| 5,772,585 A | 6/1998 | Levin et al. |
| 5,772,601 A | 6/1998 | Oka et al. |
| 5,781,442 A | 7/1998 | Engleson et al. |
| 5,794,208 A | 8/1998 | Goltra |
| 5,801,755 A | 9/1998 | Echerer |
| 5,822,544 A | 10/1998 | Chaco et al. |
| 5,823,948 A | 10/1998 | Ross, Jr. et al. |
| 5,830,150 A | 11/1998 | Palmer et al. |
| 5,832,450 A | 11/1998 | Myers et al. |
| 5,839,438 A | 11/1998 | Graettinger et al. |
| 5,842,173 A | 11/1998 | Strum et al. |
| 5,842,976 A | 12/1998 | Williamson |
| 5,842,978 A | 12/1998 | Levy |
| 5,845,255 A | 12/1998 | Mayaud |
| 5,855,550 A | 1/1999 | Lai et al. |
| 5,860,918 A | 1/1999 | Schradi et al. |
| 5,867,821 A | 2/1999 | Ballantyne et al. |
| 5,868,669 A | 2/1999 | Iliff |
| 5,899,855 A | 5/1999 | Brown |
| 5,912,656 A | 6/1999 | Tham et al. |
| 5,921,920 A | 7/1999 | Marshall et al. |
| 5,924,074 A | 7/1999 | Evans |
| 5,940,815 A | 8/1999 | Maeda et al. |
| 5,942,986 A | 8/1999 | Shabot et al. |
| 5,956,689 A | 9/1999 | Everhart, III |
| 5,970,463 A | 10/1999 | Cave et al. |
| 5,987,519 A | 11/1999 | Peifer et al. |
| 5,997,476 A * | 12/1999 | Brown ............... 600/300 |
| 6,024,699 A | 2/2000 | Surwit et al. |
| 6,047,259 A | 4/2000 | Campbell et al. |
| 6,061,657 A | 5/2000 | Whiting-O'Keefe |
| 6,093,146 A | 7/2000 | Filangeri |
| 6,101,478 A * | 8/2000 | Brown ............... 705/2 |
| 6,102,856 A | 8/2000 | Groff et al. |
| 6,112,182 A | 8/2000 | Akers et al. |
| 6,154,668 A | 11/2000 | Pedersen et al. |
| 6,168,563 B1 | 1/2001 | Brown |
| 6,206,829 B1 | 3/2001 | Iliff |
| 6,215,403 B1 | 4/2001 | Chan et al. |
| 6,225,901 B1 | 5/2001 | Kail, IV |
| 6,230,142 B1 | 5/2001 | Benigno et al. |
| 6,233,581 B1 | 5/2001 | Rambaud et al. |
| 6,234,964 B1 | 5/2001 | Iliff |
| 6,238,338 B1 | 5/2001 | DeLuca et al. |
| 6,245,013 B1 | 6/2001 | Minoz et al. |
| 6,254,536 B1 | 7/2001 | Devito |
| 6,278,999 B1 | 8/2001 | Knapp |
| 6,283,761 B1 | 9/2001 | Joao |
| 6,292,698 B1 | 9/2001 | Duffin et al. |
| 6,304,788 B1 | 10/2001 | Eady et al. |
| 6,315,719 B1 | 11/2001 | Rode et al. |
| 6,322,502 B1 | 11/2001 | Schoenberg et al. ......... 600/300 |
| 6,363,393 B1 * | 3/2002 | Ribitzky ............... 707/102 |
| 6,364,834 B1 | 4/2002 | Reuss et al. |
| 6,381,576 B1 | 4/2002 | Gilbert |
| 6,385,589 B1 | 5/2002 | Trusheim et al. |
| 6,398,728 B1 | 6/2002 | Bardy |
| 6,413,224 B1 | 7/2002 | Ogura et al. |
| 6,442,433 B1 | 8/2002 | Linberg |
| 6,463,320 B1 | 10/2002 | Xue et al. |
| 6,658,276 B2 | 12/2003 | Kianl et al. |
| 6,700,028 B2 | 3/2004 | Dryoff |
| 6,748,353 B1 | 6/2004 | Iliff |
| 6,768,999 B2 | 7/2004 | Prager et al. |
| 6,804,558 B2 | 10/2004 | Haller et al. |
| 6,893,396 B2 | 5/2005 | Schulze et al. |
| 6,941,271 B1 | 9/2005 | Soong |
| 7,039,878 B2 * | 5/2006 | Auer et al. ............... 715/810 |
| 7,374,535 B2 | 5/2008 | Schoenberg et al. |
| 7,778,851 B2 | 8/2010 | Schoenberg et al. |
| 7,831,450 B2 | 11/2010 | Schoenberg et al. |
| 7,848,935 B2 | 12/2010 | Gotlib et al. |
| 7,899,683 B2 | 3/2011 | Schoenberg et al. |
| 8,027,846 B2 | 9/2011 | Schoenberg et al. |
| 2001/0044588 A1 | 11/2001 | Mault |
| 2002/0038392 A1 | 3/2002 | De La Huerga |
| 2002/0087355 A1 | 7/2002 | Rowlandson |
| 2002/0099273 A1 | 7/2002 | Bocionek et al. |
| 2002/0173988 A1 | 11/2002 | Dang |
| 2002/0177758 A1 | 11/2002 | Schoenberg et al. |
| 2002/0177759 A1 | 11/2002 | Schoenberg et al. |
| 2002/0187483 A1 | 12/2002 | Hoffman et al. |
| 2003/0036687 A1 | 2/2003 | Schoenberg et al. |
| 2003/0163351 A1 * | 8/2003 | Brown et al. ............... 705/2 |
| 2004/0034550 A1 | 2/2004 | Menschik et al. |
| 2004/0082845 A1 | 4/2004 | Matsumoto et al. |
| 2004/0111296 A1 | 6/2004 | Rosenfeld |
| 2004/0111297 A1 | 6/2004 | Schoenberg |
| 2004/0111298 A1 | 6/2004 | Schoenberg |
| 2004/0111622 A1 | 6/2004 | Schoenberg |
| 2004/0152952 A1 | 8/2004 | Gotlib et al. |
| 2004/0153343 A1 | 8/2004 | Gotlib et al. |
| 2004/0172300 A1 | 9/2004 | Mihai et al. |
| 2004/0225629 A1 | 11/2004 | Eder |
| 2005/0055244 A1 | 3/2005 | Mullan et al. |
| 2005/0086071 A1 | 4/2005 | Fox, Jr. et al. |
| 2005/0108057 A1 | 5/2005 | Cohen et al. |
| 2005/0125256 A1 | 6/2005 | Schoenberg et al. |
| 2005/0144043 A1 | 6/2005 | Holland et al. |
| 2005/0159987 A1 | 7/2005 | Rosenfeld et al. |
| 2005/0206518 A1 | 9/2005 | Welch et al. |
| 2005/0222873 A1 | 10/2005 | Nephin et al. |
| 2005/0234739 A1 | 10/2005 | Schoenberg |
| 2005/0256815 A1 | 11/2005 | Reeve et al. |
| 2006/0004610 A1 | 1/2006 | David |
| 2007/0083111 A1 | 4/2007 | Hossack et al. |
| 2007/0125844 A1 | 6/2007 | Libin et al. |
| 2007/0162308 A1 | 7/2007 | Peters |
| 2008/0149701 A1 | 6/2008 | Lane |
| 2008/0208618 A1 | 8/2008 | Schoenberg et al. |
| 2008/0228090 A1 | 9/2008 | Wariar et al. |
| 2008/0257961 A1 | 10/2008 | Lubow |
| 2008/0306770 A1 | 12/2008 | Sysko et al. |
| 2009/0043611 A1 | 2/2009 | Nadas et al. |
| 2010/0056875 A1 | 3/2010 | Schoenberg et al. |
| 2010/0217621 A1 | 8/2010 | Schoenberg et al. |
| 2010/0217623 A1 | 8/2010 | Schoenberg et al. |
| 2010/0268552 A1 | 10/2010 | Schoenberg et al. |

FOREIGN PATENT DOCUMENTS

| | | |
|---|---|---|
| WO | WO 99/13766 | 3/1999 |
| WO | WO 00/79466 | 12/2000 |
| WO | WO 2005/067675 | 7/2005 |

OTHER PUBLICATIONS

Aukburg, S.J. et al., "Automation of Physiological Data Presentation and Alarms in the Post Anesthesia Care Unit." In Symposium on

(56) References Cited

OTHER PUBLICATIONS

Computer Applications in Medical Care, Nov. 5-8, 1989, Washington, DC; pp. 580-582.

Avila, Lorene S. and M. Michael Shabot, "Keys to the Successful Implementation of an ICU Patient Data Management System," *International Journal of Clinical Monitoring and Computing*, vol. 5, 1988, pp. 15-25.

Ayres, Stephen M. et al. Textbook of Critical Care, 3$^{rd}$ Edition, 1995, Harcourt Brace & Company. Sections IV & V.

Bates, David W. et al., "Reducing the Frequency of Errors in Medicine Using Information Technology" *Journal of the American Medical Informatics Association*, vol. 8, No. 4, Jul./Aug. 2001; pp. 299-308.

Benis, A. M. et al., "Improved Detection of Adverse Cardiovascular Trends with the Use of a Two-Variable Computer Alarm" *Critical Care Medicine*, vol. 8, No. 2, Jun. 1980: 341-344.

Berg, et al. "Remote Critical Care Consultation: Telehealth projection of clinical specialty expertise". Tripler Army Medical Center, Honolulu.

Bierman, M. I. et al., "Pulse Oximetry in the Postoperative Care of Cardiac Surgical Patients; A Randomized Controlled Trial." *Chest*, vol. 102, No. 5, Nov. 1992: 1367-1370.

Borzo, Greg, "Web Technology, Coming to a Hospital Near You," amednews.com, The Newspaper for America's Physicians, Nov. 18, 1996, Retrieved from Internet, pp. 1-4.

Bradshaw, Karen E. et al., "Development of a Computerized Laboratory Alerting System" *Computers and Biomedical Research*, vol. 22, 1989; pp. 575-587.

Bradshaw, K. E., "Computerized Alerting System Warns of Life-Threatening Events." In Symposium on Computer Application in Medical Care, Oct. 25-26, 1986, Washington, DC; pp. 403-409.

Bradshaw, Karen E. et al., "Computer-Based Data Entry for Nurses in the ICU." *M. D. Computing*, vol. 6, No. 5, 1989; pp. 274-280.

Bradshaw, Karen E. et al., "Improving Efficiency and Quality in a Computerized ICU" 1988 SCAMC, Inc., pp. 763-767.

Bradshaw, Karen E. et al., "Physician Decision Making—Evaluation of Data used in a Computerized ICU" *International Journal of Clinical Monitoring and Computing*, vol. 1, 1984; pp. 81-91.

Cannon, Scott R. and Reed M. Gardner, "Experience with a Computerized Interactive Protocol System Using HELP" *Computers and Biomedical Research*, vol. 13, 1980; pp. 399-409.

Capuano, Terry Ann et al. Remote Telemetry, Nursing Management, Vo.26, No. 7, Jul. 1995, p. 26.

Chizeck, H. J., "Modelling, Simulation and Control in a Data Rich Environment." In Symposium on Computer Applications in Medical Care, Oct. 25-26, 1986, Washington, DC; pp. 65-69.

Chu, Wesley W. et al. "A Medical Digital Library to Support Scenario and User-Tailored Information Retrieval." *Transactions on Information Technology in Biomedicine*, vol. 4, No. 2, Jun. 2000, pp. 97-107.

Clayton, P. D. et al., "Bringing HELP to the Clinical Laboratory—Use of an Expert System to Provide Automatic Interpretation of Laboratory Data" *Ann Clin Biochem*, vol. 24, Supplement, 1987; pp. S1-5 to S1-11.

Clayton, P.D. et al., "Data Driven Interpretation of Laboratory Results in the Context of a Medical Decision Support System" *Clinical Biochemistry, Principles-Methods, Applications 2*, Data Presentation Interpretation (Eds. H. Keller and Ch. Trendelenburg), Walter deGruyter, Berlin—New York, 1989; Chapter 3.7; pp. 367-380.

Clemmer, T. P. et al, "Computer Support in Critical Care Medicine" Proceedings of the Fourth Annual Symposium on Computer Applications in Medical Care, Part III, Nov. 2-5, 1980, Washington, D.C.; pp. 1557-1561.

Clemmer, Terry P. and Reed M. Gardner, "Data Gathering, Analysis, and Display in Critical Care Medicine" *Respiratory Care*, vol. 30, No. 7, Jul. 1985; pp. 586-601.

Clemmer, Terry P. and Reed M. Gardner, "Medical Informatics in the Intensive Care Unit: State of the Art 1991" *International Journal of Clinical Monitoring and Computing*, vol. 8, 1992; pp. 237-250.

Coiera, E., "Intelligent Monitoring and Control of Dynamic Physiological Systems." *Artificial Intelligence in Medicine*, vol. 5, 1993: pp. 1-8.

Colvin, J. R. et al., "Microcomputer-Controlled Administration of Vasodilators Following Cardiac Surgery: Technical Considerations." *J. Cardiothoracic Anesthesia*, vol. 3, No. 1, Feb. 1989: pp. 10-15.

Coplin, W. M. et al., "Accuracy of Continuous Jugular Bulb Oximetry in the Intensive Care Unit." Neurosurgy, vol. 42, No. 3, Mar. 1998: 533-540.

Crew, A. D. et al., "Preliminary Clinical Trials of a Computer-Based Cardiac Arrest Alarm." Intensive Care Med, vol. 17, 1991: 359-364.

DeLima, Marie et al., "Successful Implementation of a Multiple-ICU Clinical Information System in a Tertiary Care Medical Center" AMIA 2000 Annual Symposium; Session S62—Poster Session 2.

de Oliveira, Guedes P. et al., "The Role of Computer Based Techniques in Patient Monitoring: Technical Note." *Acta Neuorchir*, vol. 55, 1992 (Suppl.): 18-20.

Doctors use 'remote control' to monitor ICU patients, CNN.com. technology>computing, Aug. 21, 2000, http://www.cnn.com/2000/TECH/computing/08/21/icu..t_t/.

Duncan, Ray and Jeffrey J. Pomerance, "Computer Assistance in Delivery of Patient Care in a Neonatal Intensive Care Unit," *The Use of Computers in Perinatal Medicine*, Chapter 19, Abstract only, 1982, Retrieved online from: Neonatology on the Web.

Duncan, Ray, "Computer Assisted Care in the Neonatal Intensive Care Unit," *The Use of Computers in Perinatal Medicine*, Proceedings of the 17$^{th}$ Annual Symposium on Computer Applications in Medical Care, American Medical Informatics Association, Abstract only, Nov. 1993, Retrieved online from: Neonatology on the Web.

East, T. D. et al., "A Strategy for Development of Computerized Critical Care Decision Support Systems," *Int J Clin Monit Comput*, vol. 8, No. 4, Abstract only, 1991-1992, Retrieved online from: PubMed.

East, Thomas D. et al., "Computers in Critical Care" *Critical Care Nursing Clinics of North America*, vol. 7, No. 2, Jun. 1995; pp. 203-216.

East, Thomas D. et al., "Development of Computerized Critical Care Protocols—A Strategy That Really Works!" Proceedings of 14$^{th}$ Symposium on Computer Applications in Medical Care, 1990; pp. 564-568.

East, Thomas D. et al., "Digital Electronic Communication between ICU Ventilators and Computers and Printers" *Respiratory Care*, vol. 37, No. 9, Sep. 1992; pp. 1113-1123.

East, Thomas D. et al., "Implementation Issues and Challenges for Computerized Clinical Protocols for Management of Mechanical Ventilation in ARDS Patients" SCAMC 1989: 13: 583-587.

Elliott, C. Gregory et al., "Computer-assisted Medical Direction of Respiratory Care" *Respiratory Management*, vol. 19, No. 2, 1989; pp. 31-35.

Evans, R. Scott et al., "A Computerized Approach to Monitor Prophylactic Antibiotics" 1987 SCAMC, Inc., 241-245.

Evans, R. Scott et al., "Computer Surveillance of Hospital-Acquired Infections and Antibiotic Use" *JAMA*, vol. 256, No. 8, Aug. 22/29, 1986; pp. 1007-1011.

Evans, R. Scott et al., "Development of a Computerized Adverse Drug Event Monitor" Proc Annu Symp Comput Appl Med Care. 1991; pp. 23-27.

Evans, R. Scott et al., "Development of a Computerized Infectious Disease Monitor (CIDM)" *Computers and Biomedical Research*, vol. 18, 1985; pp. 103-113.

Evans, R. Scott et al., "Prediction of Hospital Infections and Selection of Antibiotics Using and Automated Hospital Database." 1990 SCAMC, Inc.; pp. 663-667.

Evans, R. Scott et al., "Reducing the Duration of Prophylactic Antibiotic Use Through Computer Monitoring of Surgical Patients" *DICP, The Annals of Pharmacotherapy*, vol. 24, Apr. 1990; pp. 351-354.

Factor, Michael et al., "Real-Time Data Fusion in the Intensive Care Unit," *IEEE. Computer*, Abstract only, Nov. 1991, Retrieved online from: Neonatology on the Web.

Fischer, Joachim E. et al., "Quantifying Uncertainty: Physicians' Estimates of Infection in Critically Ill Neonates and Children" *CID*, vol. 38, May 15, 2004; pp. 1383-1390.

(56) References Cited

OTHER PUBLICATIONS

Fitzpatrick, Geraldine, "TARDIS Evaluation, Report on Final Usage Evaluation of the TARDIS Telehealth System" Distributed Systems Technology Centre, DSTC Pty. Ltd., Jul. 24, 1998; pp. 1-54.

Fleegler et al. "Apache III, Equation Update—version III-I ("eye")(Note: Includes Validation of Mortality Equations Carried Over to Version III-J)" White Paper Report, Aug. 1998, Cerner Corporation; pp. 1-13.

Fleegler et al. "Apache III, Equation Update (Version III-J)" White Paper Report, Oct. 2002, Cerner Corporation; pp. 1-22.

Frize, Monique and Robin Walker, "Clinical Decision-Support Systems for Intensive Care Units Using Case-Based Reasoning" *Med Eng Phys*, vol. 22, No. 9, 2000; pp. 671-677.

Fumai, N. et al., "Database Design of an Intensive Care Unit Patient Data Management System," *Proceedings of the Fourth Annual IEEE Symposium on Computer-Based Medical Systems*, Abstract only, IEEE Computer Society Press, Los Alamitos, CA, May 12, 1991, Retrieved online from: Neonatology on the Web.

Furst, Emmanuel, "Cardiovascular Technology" *J Cardiovasc Nurs*, vol. 4, No. 1, 1989; pp. 68-78.

Galfalvy, H.C. et al., "Evaluation of Community Care Network (CCN) System in a Rural Health Care Setting" 1995 AMIA, Inc.; pp. 698-702.

Gardner, R.M, "Computers in the ICU and Surgery-Keeping Real-Time Patient Records for Decision-Making." pp. 151-157.

Gardner, Reed M, "Computerized Management of Intensive Care Patients," *M.D. Computing*, vol. 3, No. 1, Abstract only, 1986, Retrieved online from: Neonatology on the Web.

Gardner, Reed M. "Integrated Computerized Records Provide Improved Quality of Care with Little Loss of Privacy" *Journal of the American Medical Informatics Association*, vol. 1, No. 4, Jul./Aug. 1994; pp. 320-322.

Gardner, Reed M. and Karen W. Hollingsworth, "ECG and Pressure Monitoring: How to Obtain Optimal Results" The Society of Critical Care Medicine: Textbook of Critical Care, Second Edition, W.B. Saunders, Co.: Philadelphia, PA, USA, 1989; Chapter 33; pp. 295-305.

Gardner, Reed M. and M. Michael Shabot, "Computerized ICU Data Management: Pitfalls and Promises" *International Journal of Clinical Monitoring and Computing*, vol. 7, 1990; pp. 99-105.

Gardner, Reed M. and M. Michael Shabot, "Computerized ICU Data Management: Pitfalls and Promises," *International Journal of Clinical Monitoring and Computing*, vol. 7, Abstract only, 1990, Retrieved online from: Neonatology on the Web.

Gardner, Reed M. and R. Scott Evans, "Computer-Assisted Quality Assurance" *Group Practical Journal*, vol. 41, No. 3., May/Jun. 1992; pp. 8-11.

Gardner, Reed M. and Terry P. Clemmer, "Computerized Protocols Applied to Acute Patient Care" *Advances in Automated Analysis*, vol. 1, Technicon International Congress 1976, Mediad Incorporated, Tarrytown, NY; pp. 158-193.

Gardner, Reed M. and William L. Hawley, "Standardizing Communications and Networks in the ICU" Patient Monitoring and Data Management, *Managing Patient Data*, 1985 AAMI; pp. 59-63.

Gardner, Reed M. et al, "Integrated Computer Systems for Monitoring of the Critically Ill" Proc. Comput. Appl. Med. Care, 1977, pp. 301-307.

Gardner, Reed M. et al., "Assessing the Effectiveness of a Computerized Pharmacy System" Proceedings of the Fourteenth Annual Symposium on Computer Applications in Medical Care, Washington, DC, Nov. 4-7, 1990; pp. 668-672.

Gardner, Reed M. et al., "Computer-based ICU Data Acquisition as an Aid to Clinical Decision-Making" *Critical Care Medicine*, vol. 10, No. 12, Dec. 1982; pp. 823-830.

Gardner, Reed M. et al., "Computer-Critiqued Blood Ordering Using the HELP System" *Computers and Biomedical Research*, vol. 23, 1990; pp. 514-528.

Gardner, Reed M. et al., "Computerized Blood Gas Interpretation and Reporting System" *Computer Magazine*, Jan. 1975; pp. 39-45.

Gardner, Reed M. et al., "Computerized Medical Care: The HELP System at LDS Hospital" *Journal of AHIMA*, vol. 63, No. 6, 1992; pp. 68-78.

Gardner, Reed M. et al., "Computers in the Emergency Room" *Internal Medicine for the Specialist*, vol. 8, No. 3, Mar. 1987; pp. 105-114.

Gardner, Reed M. et al., "Computers in the Intensive Care Unit: A Match Meant to Be!" *Textbook of Critical Care*, Chapter 196, Third Edition, W.B. Saunders Company, 1995; pp. 1757-1770.

Gardner, Reed M. et al., "Computers in the Intensive Care Unit: Match or Mismatch?" The Society of Critical Care Medicine: Textbook of Critical Care, Second Edition, W.B. Saunders, Co.: Philadelphia, PA, USA, 1989; Chapter 26: pp. 248-259.

Gardner, Reed M. et al., "Distributed Data Base and Network for ICU Monitoring" IEEE Computers in Cardiology, Salt Lake City, Utah, Sep. 18-24, 1984; pp. 305-307.

Gardner, Reed M. et al., "Eight-Channel Data Set for Clinical EEG Transmission Over Dial-Up Telephone Network" IEEE Transactions on Biomedical Engineering, vol. BME-21, No. 3, May 1974; pp. 246-249.

Gardner, Reed M. et al., "Integrated Computer Network for Acute Patient Care" Proceedings of 1984 Symposium on Computer Applications in Medical Care, Nov. 4-7, 1984, Washington, D.C.; pp. 185-188.

Gardner, Reed M. et al., "Monitoring Direct Blood Pressure: Algorithm Enhancements" IEEE Comput Cardiol 1986;13:607-610.

Gardner, Reed M. et al., "Real Time Data Acquisition: Experience With the Medical Information Bus (MIB)" Proc Annu Symp Comput Appl Med Care. 1991; pp. 813-817.

Gardner, Reed M. et al., "The HELP Hospital Information System: Update 1998," *International Journal of Medical Informatics*, vol. 54, pp. 169-182, 1999.

Gardner, Reed M., "Computerized Alert System Use in Clinical Medicine" 1979 IEEE, pp. 136-140.

Gardner, Reed M., "Computerized Data Management and Decision Making in Critical Care" Symposium on Critical Care, *Surgical Clinics of North America*, vol. 65, No. 4, Aug. 1985; pp. 1041-1051.

Gardner, Reed M., "Computerized Intensive Care Monitoring at LDS Hospital—Progress and Development" IEEE-NIH Conference on Computers in Cardiology, Oct. 1974; pp. 97-105.

Gardner, Reed M., "Computerized Management of Intensive Care Patients" *Images, Signals and Devices*, vol. 3, No. 1, 1986; pp. 36-51.

Gardner, Reed M., "Computerized Patient Monitoring at LDS Hospital—An Evaluation" Proceedings of the San Diego Biomedical Symposium, 1971; vol. 10; pp. 151-159.

Gardner, Reed M., "Computers in Critical Care" *Wellcome Trends in Hospital Pharmacy*, Jul. 1992; p. 6-8.

Gardner, Reed M., "Computers in the ICU" *Medical Electronics*, Jun. 1984; pp. 129-135.

Gardner, Reed M., "Information Management—Hemodynamic Monitoring" *Seminars in Anesthesia*, vol. II, No. 4, Dec. 1983; pp. 287-299.

Gardner, Reed M., "Monitoring of Physiological Data in a Clinical Environment" Annual Review of Biophysics and Bioengineering, vol. 1, 1972; pp. 211-224.

Gardner, Reed M., "Patient-Monitoring Systems" Medical informatics: computer applications in health care table of contents, Chapter 12, pp. 366-399. Wesley Longman Publishing Co., Inc. Boston, MA, USA, 1990.

Gardner, Reed M., "Tomorrow's Electronic Hospital is Here Today" *IEEE Spectrum*, Jun. 1984; pp. 101-103.

Gardner, Reed M. "Performance of Computerized Protocols for the Management of Arterial Oxygenation in an Intensive Care Unit," International Journal of Clinical Monitoring and Computing 8, 1992, 271-180, Kluwer Academic Publishers, Netherlands.

Garfinkel D. et al., "Patient Monitoring in the Operating Room: Validation of Instrument Reading by Artificial Intelligence Methods." In Symposium on Computer Applications in Medical Care, Nov. 5-8, 1989, Washington, DC; pp. 575-579.

Garfinkel, D. et al., "PONI: An Intelligent Alarm System for Respiratory and Circulation Management in the Operating Rooms." In Symposium on Computer Applications in Medical Care, Nov. 6-9, 1988, Washington, DC; pp. 13-17.

(56) References Cited

OTHER PUBLICATIONS

Gray, J.E. et al., "Baby CareLink: Using the Internet and Telemedicine to Improve Care for High-risk Infants," *Pediatrics*, vol. 106, No. 6, Abstract only, Dec. 2000, Retrieved online from: Neonatology on the Web.

Grundy, Betty L. et al., "Telemedicine in Critical Care: An Experiment in Health Care Delivery" *JACEP*, vol. 6, No. 10., Oct. 1977; pp. 439-444.

Grundy, Betty Lou et al., "Telemedicine in Critical Care: Problems in Design, Implementation, and Assessment" *Critical Care Medicine*, vol. 10, No. 7, Jul. 1982; pp. 471-475.

Hahnel, J. et al., "Can a Clinician Predict the Technical Equipment a Patient will Need During Intensive Care Unit Treatment? An Approach to Standardize and Redesign the Intensive Care Unit Workstation." *J. Clinical Monitoring*, vol. 8, No. 1, Jan. 1992: 1-6.

Hall, G. L. & P.B. Colditz, "Continuous Physiological Monitoring: An Integrated System for Use in Neonatal Intensive Care." *Australian Physical & Engineering Sciences in Medicine*, vol. 18, No. 3, 1995; 139-142.

Halpern, Neil A. et al., "Critical Care Medicine in the United States 1985-2000: An Analysis of Bed Numbers, Use, and Costs" *Crit Care Med*, vol. 32, No. 6, 2004; pp. 1254-1259.

Haug, Peter J. et al., "Decision Support in Medicine: Examples from the HELP System" *Computers and Biomedical Research*, vol. 27, 1994: pp. 396-418.

Haug, Peter J. et al., "Hospital-Based Decision Support," *Clinical Decision Support Systems, Theory and Practice*, Springer-Verlag New York Inc., 1994; pp. 77-103.

Hayes-Roth, B. et al., "Guardian: An Experimental System for Intelligent ICU Monitoring." In Symposium on Computer Applications in Medical Care, Nov. 5-9, 1994, Washington, DC; p. 1004.

Henderson, Susan E. et al., "Computerized Clinical Protocols in an Intensive Care Unit: How Well Are They Followed?" 1990 SCAMC, Inc.; 284-288.

Henderson, Susan et al., "Performance Evaluation of Computerized Clinical Protocols for Management of Arterial Hypoxemia in ARDS Patients" Proc. 13th Annual Symp. Comput. Appl. Med. Care. 1989. Washington, D.C., pp. 588-592.

Henderson, Susan et al., "Performance of Computerized Protocols for the Management of Arterial Oxygenation in an Intensive Care Unit" *International Journal of Clinical Monitoring and Computing*, vol. 8, 1992; pp. 271-280.

Henkind, S.J., et al., "A Clinical Alarm System Using Techniques from Artificial Intelligence and Fuzzy Set Theory," *Approximate Reasoning in Intelligent Systems, Decision and Control*, Pergamon Press, 1987, pp. 91-104.

Henkind, Steven et al. "Intensive Care Unit Monitoring Using a Real-Time Expert System," *Computers in Cardiology*, Sep. 18-21, Salt Lake City, Utah, 1994, pp. 7-12.

Heterington. "High tech meets high touch: telemedicine's contribution to patient wellness". Nursing Administration Quarterly, 22(3), Spring 1998.

Hosseinzadeh, Abolfazl, "A Rule-Based System for Vital Sign Monitoring in Intensive Care", Department of Electrical Engineering, McGill University, Montreal; Nov. 1993.

Hripcsak, George et al., "Design of a Clinical Event Monitor," *Computers and Biomedical Research*, vol. 29, No. 3, Abstract only, Jun. 1996, Retrieved online from: Neonatology on the Web.

Hulse, Russell K. et al., "Computerized Medication Monitoring System" *American Journal of Hospital Pharmacy*, vol. 33, Oct. 1976; pp. 1061-1064.

Ingenerf, Josef. "Telemedicine and Terminology: Different Needs of Context Information." *Transactions on Information Technology in Biomedicine*, vol. 3, No. 2, Jun. 1999, pp. 92-100.

Irazurta, Jose, "Monitoring in Pediatric Intensive Care." *Indian J Pediatrics*, vol. 60, 1993: 55-65.

Jamzad et al. "A human friendly reporting and database system for brain PET analysis" Annals of Nuclear Medicine 10(1):99-104, 1996.

Janofsky, Michael, "Finding Value in Intensive Care, from Afar," The New York Times on the Web, Jul. 27, 1999, www.Visicu.com/companynews/0799_nytimes.htm.

Jans, R. et al., "A Low Cost ECG Central Station for Intensive Care." *Australian Physical & Engineering Sciences in Medicine*, vol. 13, No. 1, 1990: 31-35.

Jastremski, M. et al., "A Model for Technology Assessment as Applied to Closed Loop Infusion Systems." *Critical Care Medicine*, vol. 23, No. 10, Oct. 1995: 1745-1755.

Johnson, Bob et al., *Discern—An Integrated Prospective Decision Support System*, Symposium on Computer Applications in Medical Care. A Conference of the American Medical Informatics Associated, Nov. 5-19, 1994, Washington, D.C. p. 969.

Johnson, Dickey Seidlitz et al., "A Computerized Alert Program for Acutely Ill Patients" *Journal of Nursing Administration*, Jun. 1980; pp. 26-35,.

Kaplan, Simon M. et al. Designing Support for Remote Intensive-Care Telehealth Using the Locales Framework, ACM, 1997, 99.173-184.

Kassirer, Jerome P., "The Next Transformation in the Delivery of Health Care (Editorial)," *NEJM*, vol. 332, No. 1, Abstract only, Jan. 5, 1995, Retrieved online from: Neonatology on the Web.

Keller, H. et al. Data Presentation Interpretation, Clinical Biochemistry Principles, Methods, Applications, Walter-deGruyter & Co., 1989.

Kimura, Michio et al. "MERIT-9: a patient information exchange guideline using MML, HL7, and DICOM." International Journal of Medical Informatics, vol. 51, No. 1, Jul. 1998, pp. 59-68.

Klaas, M. A. & E. Y. Cheng, "Early Response to Pulse Oximetry Alarms with Telemetry." *J. Clinical Monitoring*, vol. 10, No. 3, May 1994: 178-180.

Kleinholz, Lutz et al. "Supporting Cooperative Medicine: the Bermed Project." *IEEE Multimedia*, vol. 1, No. 4, Dec. 1994, pp. 44-53.

Kohane, I. S. et al., "Hypothesis-Driven Data Abstraction with Trend Templates." In Symposium on Computer Applications in Medical Care, Oct. 30-Nov. 3, 1993, Washington, DC; pp. 444-448.

Kontaxis, K.M. et al. "Using XML and Controlled Vocabularies to Achieve Unambiguous Knowledge Acquistion From Multiple Hetereogeneous Medical Data Sources." *Information Technology Applications in Biomedicine*, 4th International IEEE EMBS Special Topic Conference on Apr. 24-26, 2003, pp. 161-164.

Koski, E. M. J. et al., "A Knowledge-Based Alarm System for Monitoring Cardiac Operated Patients—Assessment of Clinical Performance." *International J. Clinical Monitoring and Computing*, vol. 11, 1994: 79-83.

Koski, E. M. J. et al., "Development of an Expert System for Haemodynamic Monitoring: Computerized Symbolism of On-Line Monitoring Data." *International J Clinical Monitoring and Computing*, vol. 8, 1992: 289-293.

Kostopoulou, O. and M. Wildman, "Sources of Variability in Uncertain Medical Decisions in the ICU: a Process Tracing Study" *Qual Saf Health Care*, vol. 13, 2004; pp. 272-280.

Kuperman, Gil et al., "Continuous Quality Improvement Applied to Medical Care: Experiences at LDS Hospital" *Medical Decision Making*, vol. 11, No. 4, Oct.-Dec. 1991 Supplement; pp. S60- S65.

Kuperman, Gilad J. & Reed M. Gardner, "The Help System. A Snapshot in Time." Department of Biophysics, LDS Hospital, Salt Lake City, Utah, Sep. 1988; pp. 1-295.

Kuperman, Gilad J. et al., "Clinical Decision Support for Hospital and Critical Care" *Journal of Healthcare Information Management*, vol. 13, No. 2, Summer 1999; pp. 81-96.

Kuperman, Gilad J., Reed M. Gardner and T. Allan Pryor, "HELP: A Dynamic Hospital Information Systems," *Computer and Medicine*, Springer-Verlag New York Inc., 1991; 174 pages (unnumbered).

L'Estrange, P. R. et al., "A Microcomputer System for Physiological Data Collection and Analysis." *Australian Dental Journal*, vol. 38, No. 5, Oct. 1993: 400-405.

Laffel, G. et al., "Using Control Charts to Analyze Serial Patient-Related Data." *Quality Management in Health Care*, vol. 3, No. 1, Fall 1994: 70-77.

(56) References Cited

OTHER PUBLICATIONS

Larsen, Robert A. et al., "Improved Perioperative Antibiotic Use and Reduced Surgical Wound Infections Through Use of Computer Decision Analysis." *Infect Control Hosp Epidemiol*, vol. 10, No. 7, 1989; pp. 316-320.

Laurenson, R.C., "Computer Software 'Article of Manufacture' Patents," *JPTOS*,:811-824 (1995) Previously appeared in *Computer Law Reporter*, 21(6):965-974 (1995).

Lee, Ho Sung et al., "Remote Patient Monitoring Service through World-Wide Web" Proceedings—19th International Conference—IEEE/EMBS Oct. 30-Nov. 2, Chicago, IL. USA; pp. 928-931.

Lepage, E. et al., "Development of a Computerized Knowledge Based System Integrated to a Medical Workstation: Application to Blood Transfusion" IMIA 1992; pp. 585-590.

Lepage, Eric F. et al., "Assessing the Effectiveness of a Computerized Blood Order "Consultation" System" 1992 AMIA, Inc.; pp. 33-37.

Lewis, F. John et al., "Continuous Patient Monitoring with a Small Digital Computer," *Computers and Biomedical Research*, vol. 5, Abstract only, 1972, Retrieved online from: Neonatology on the Web.

Leyerle, Beverley J. et al., "Integrated Computerized Databases for Medical Data Management Beyond the Bedside" *International Journal of Clinical Monitoring and Computing*, vol. 7, 1990, pp. 83-89.

Leyerle, Beverley J. et al., "The PDMS as a Focal Point for Distributed Patient Data." *International Journal of Clinical Monitoring and Computing*, vol. 5, 1988. pp. 155-161.

Li, Xin et al., "A World Wide Web Telemedicine System" *SPIE*, vol. 2711, 1996; pp. 427-439.

Litt et al. "Graphical representation of medical information in the visual chart" Proceedings, 1994 IEEE Seventh Symposium on Computer-based Medical Systems, pp. 252-257, Jun. 11-12, 1994.

M. de Beer, N. A. et al., "Clinical Evaluation of a Method for Automatic Detection and Removal of Artifacts in Auditory Evoked Potential Monitoring." *J. Clinical Monitoring*, vol. 11, No. 6, Nov. 1995: 381-391.

Mabry, Susan L. et al., Integrated Medical Analysis System, Proceedings of the 1997 Winter Simlation Conference, 1997, pp. 1167-1168.

Major, Kevin et al., "Wireless Clinical Alerts and Patient Outcomes in the Surgical Intensive Care Unit." *The American Surgeon*, vol. 68, Dec. 2002; pp. 1057-1060.

Makivirta, A. & E. M. J. Koski, "Alarm-Inducing Variability in Cardiac Postoperative Data and the Effects of Prealarm Delay." Critical Care Medicine, vol. 8, No. 6, May 1994: 153-162.

Makivirta, A. et al., "The Median Filter as a Preprocessor for a Patient Monitor Limit Alarm System in Intensive Care." *Computer Methods and Programs in Biomedicine*, vol. 34, No. 2/3, Feb./Mar. 1991: 139-144.

Martin, J. F., "Closed-Loop Control of Arterial Pressure During Cardiac Surgery." J. Clinical Monitoring, vol. 8, No. 3, Jul. 1992: 252-253.

McDonald, CJ, "Protocol-Based Computer Reminders, the Quality of Care and the Non-Perfectibility of Man," *The New England Journal of Medicine*, vol. 295, No. 24, Abstract only, Dec. 9, 1976, Retrieved online from: Science Library.

McDonald, Clement J. and William M. Tierney, "Computer-Stored Medical Records, Their Future Role in Medical Practice," *Jama*, vol. 259, No. 23, pp. 3433-3440; Jun. 17, 1988.

Merz, U. et al., "Computer-Assisted Monitoring in the Neonatal Intensive Care Unit [German]," *Klin Padiatr*, vol. 207, No. 6, Abstract only, Nov./Dec. 1995, Retrieved online from: Neonatology on the Web.

Metnitz, P.G. et al., "Computer Assisted Data Analysis in Intensive Care: the ICDEB Project—Development of a Scientific Database System for Intensive Care (Intensive Care Data Evaluation Project)" *Int J Clin Monit Comput*, vol. 12, No. 3, Abstract only, 1995, Retrieved online from: Neonatology on the Web.

Meyer, C., "Visions of Tomorrow's ICU." *American J. Nursing*, Apr. 1993: 27-31.

Microsoft Press Computer Dictionary, Third Edition, 1997, p. 430.

Microsoft Support Document 236963 describing the functionality of the Windows 95 OS.

Miksch, Silvia. Artificial Intelligence for Decision Support: Needs Possibilities, and Limitations in ICU, 10th Postgraduate Course in Critical Care Medicine APICE '95, Springer, 1995.

Miller, Randolph A. et al., "Summary Recommendation for Responsible Monitoring and Regulation of Clinical Software Systems," *Annals of Internal Medicine*, vol. 127, No. 9, pp. 842-845, Nov. 1, 1997.

Morales, A. Alfredo et al., "An Application Server Approach for Integration of Clinical Systems," *Proceedings of the AMIA 1999 Annual Symposium*, Abstract only, Amia, 1999, Retrieved online from: Neonatology on the Web.

Mrus, Joseph M., "Getting Beyond Diagnostic Accuracy: Moving toward Approaches That Can be Used in Practice" *CID*, Editorial Commentary, vol. 38, May 15, 2004; pp. 1391-1393.

Nelson, Russell M. et al., "Computer Based Monitoring of Patients Following Cardiac Surgery" *Computers in Cardiology*, vol. 5, No. 4, Jul.-Aug. 1969; pp. 926-930.

Nenov, V. I. et al., "Computer Applications in the Intensive Care Unit." *Neurosurgery Clinics of North America*, vol. 5, No. 4, Oct. 1994: 811-827.

Nenov, Valeriy et al. Remote Access to Neurosurgical ICU Physiological Data using the World Wide Web, Health Care in the Information Age, 1996, pp. 242-249.

Nobel, J. J., "Physiologic Monitoring Systems, Acute Care." *Pediatric Emergency Care*, vol. 8, No. 4, Aug. 1992: 235-237.

Norris, Patrick R. et al., "Web-Based Data Integration and Annotation in the Intensive Care Unit." Proc AMIA Annu Fall Symp. 1997; pp. 794-798.

Nossister. Using Excel 5 for Windows (The User Friendly Reference), Copyright 1995, by Que Corporation.

Oliver, Suzanne, "Take Two Aspirin; The Computer will Call in the Morning." *Forbes*, Mar. 14, 1994. pp. 110-111.

On, J. A. & Westenskow, D. R., "A Breathing Circuit Alarm System Based on Neural Networks." *J. Clinical Monitoring*, vol. 10, No. 2, Mar. 1994: 101-109.

Palley, N. A., et al. "Programming in the Medical Real-Time Environment." *AFIPS Conference Proceedings, vol. 37, Fall Joint Computer Conference*, Nov. 17-19, 1970, Houston Texas. pp. 589-598.

Pappert, D. et al., "Preliminary Evaluation of a New Continuous Intra-Arterial Blood Gas Monitoring Device." *Acta Anaesthesiologica Scandinavica*, Suppl. 107, vol. 39, 1995: 67-70.

Perednia, Douglas A. Telemedine Technology and Clinical Applications, JAMA, vol. 6, Feb. 8, 1995, p. 483.

Perlstein, Paul H. et al., "Computer Assisted Newborn Intensive Care," *Pediatrics*, vol. 57, No. 4, Abstract only, Apr. 1976, Retrieved online from: Neonatology on the Web.

Pestotnik, Stanley L. et al., "Therapeutic Antibiotic Monitoring: Surveillance Using a Computerized Expert System" *The American Journal of Medicine*, vol. 88, 1990; pp. 43-48.

Pryor, T. A. et al., "The Help System" 1982 IEEE, pp. 19-27.

Pryor, T. A. et al., "The HELP System" *Journal of Medical Systems*, vol. 7, No. 2, 1983; pp. 87-102.

Pryor, T. Allan et al., "A Distributed Processing System for Patient Management" 1978 IEEE, *Computers in Cardiology*, Sep. 1978; pp. 325-328.

Pryor, T. Allan et al., "Computer System for Research and Clinical Application to Medicine" Fall Joint Computer Conference, 1968; Reprinted from AFIPS—Conference Proceedings, vol. 33, 1968; pp. 809-816.

Pryor, T. Allan et al., "HELP—A Hospital—Wide System for Computer-Based Support of Decision-Making" pp. 1-14 (unnumbered).

Pryor, T. Allan et al., "HELP—A Total Hospital Information System" Proceedings of the Fourth Annual Symposium on Computer Applications in Medical Care, Part I, Nov. 2-5, 1980, Washington, D.C.; pp. 3-7.

PTO Decision on Re-examination for Patent No. 6,804,656.

Rampil, I. J., "Intelligent Detection of Artifact." *The Automated Anesthesia Record and Alarm Systems*, Chapter 17, 1987: 175-190.

Reddy, Dr. Ramana & Dr. V. "Juggy" Jagannathan, "Final Report" *Secure Collaboration for Technology for Rural Clinical Telemedicine*, Contract No. N01-LM-6-3549, Submitted by: West Virginia Research Corporation, Concurrent Engineering Research

(56) References Cited

OTHER PUBLICATIONS

Center, West Virginia University, Morgantown, WV, Submitted to: The National Library of Medicine, Copyright © 1999 West Virginia University; pp. 1-77.
Reddy, Dr. Ramana & Dr. V. "Juggy" Jagannathan, "Phase 1 Quarterly Report, Apr. 1-Jun. 30, 1997" *Secure Collaboration for Technology for Rural Clinical Telemedicine*, Funded by the National Library of Medicine, Copyright © 1999 West Virginia University; Retrieved from Internet, pp. 1-5.
Reddy, Dr. Ramana & Dr. V. "Juggy" Jagannathan, "Phase 1 Quarterly Report, Jan. 1-Mar. 1, 1997" *Secure Collaboration for Technology for Rural Clinical Telemedicine*, Funded by the National Library of Medicine, Copyright © 1999 West Virginia University; Retrieved from Internet, pp. 1-5.
Reddy, Dr. Ramana & Dr. V. "Juggy" Jagannathan, "Phase 1 Quarterly Report, Sep. 1-Dec. 1, 1996" *Secure Collaboration for Technology for Rural Clinical Telemedicine*, Funded by the National Library of Medicine, Copyright © 1999 West Virginia University; Retrieved from Internet, pp. 1-5.
Reddy, Dr. Ramana & Dr. V. "Juggy" Jagannathan, "Project Summary; Telemedicine Team" *Secure Collaboration for Technology for Rural Clinical Telemedicine*, Funded by the National Library of Medicine, Copyright © 1999 West Virginia University; Retrieved from Internet, pp. 1-12.
Remote Monitoring of ICU Patients Lowers Mortality Rates, Complications, Johns Hopkins Newsrelease, Mar. 20, 2001, http://www.newswise.com/areticles/2001/3/ICU.JHM.html.
Reddy, S. et al., "Experiences with ARTEMIS—An Internet-Based Telemedicine System" 1997 AMIA, Inc.; pp. 759-763.
Rind, David M. et al., "Designing Studies of Computer-Based Alerts and Reminders," *M.D. Computing*, vol. 12, No. 2, Abstract only, 1995, Retrieved online from: Neonatology on the Web.
Rind, David M., et al., "Effect of Computer-Based Alerts on the Treatment and Outcomes of Hospitalized Patients," *Archives of Internal Medicine*, Vo. 154, Jul. 11, 1994, pp. 1511-1517.
Rocha, Beatriz H.S.C. et al., "Computerized Detection of Nosocomial Infections in Newborns," In Symposium on Computer Applications in Medical Care, Nov. 5-9, 1994, Washington, DC; pp. 684-688.
Rosenfeld, M.D., Brian A. FCCM, FCCP, et al., Intensive care unit telemedicine: Alternate paradigm for providing continuous intensivist care, Critical Care Medicine, vol. 28, No. 12, 2000 p. 3925.
Runciman, W. B. et al., "The Pulse Oximeter: Applications and Limitations—An Analysis of 2000 Incident Reports." *Anaesthesia and Intensive Care*, vol. 21, No. 5, Oct. 1993: 543-550.
Safran, Charles et al., "Computer-Based Support for Clinical Decision Making," *M.D. Computing*, vol. 7, No. 5, Abstract only, 1990, Retrieved online from: Neonatology on the Web.
Sailors, R. M., "A Model-Based Simulator for Testing Rule-Based Decision Support Systems for Mechanical Ventilation of ARDS Patients." In Symposium on Computer Applications in Medical Care, Nov. 5-9, 1994, Washington, DC; p. 1007.
Sanklecha, M., "The Pulse Oximeter." *Indian J. Pediatrics*, vol. 60, No. 3, 1993: 469-470.
Schnapp, L. M. & N. J. Cohen, "Pulse Oximetry; Uses and Abuses." *Chest*, vol. 98, No. 5, Nov. 1990: 1244-1250.
Seiver, Adam, "ICU Bedside Technology, Critical Care Computing, Past, Present, and Future" *Critical Care Clinics*, vol. 16, No. 4, Oct. 2000; pp. 1-17. Retrieved from Internet on Oct. 13, 2003.
Shabot, M. M. et al., "Decision Support Alerts for Clinical Laboratory and Blood Gas Data" *International Journal of Clinical Monitoring and Computing*, vol. 7, 1990, pp. 27-31.
Shabot, M. Michael & Reed M. Gardner, "Decision Support Systems in Critical Care." *Computers and Medicine*, Springer-Verlag New York Inc., 1994; pp. 1-419.
Shabot, M. Michael and Mark LoBue, "Cedars-Sinai Medical Center Critical Alerting System" Cedars-Sinai Medical Center, Feb. 2004; pp. 1-16.
Shabot, M. Michael and Mark LoBue, "Real-Time Wireless Decision Support Alerts on a Palmtop PDA" 1995 AMIA, Inc., pp. 174-177.
Shabot, M. Michael et al., "Inferencing Strategies for Automated ALERTS on Critically Abnormal Laboratory and Blood Gas Data" 1989 SCAMC, Inc.; pp. 54-57.
Shabot, Michael M. et al., "Automatic Extraction of Intensity-Intervention Scores From a Computerized Surgical Intensive Care Unit Flowsheet" *The American Journal of Surgery*, vol. 154, Jul. 1987; pp. 72-78.
Shabot, Michael M. et al., "Wireless Clinical Alerts for Physiologic, Laboratory and Medication Data" Proceedings of the American Medical Informatics Association Annual Symposium, 2000; pp. 789-793.
Shortliffe, Edward H., "Computer Programs to Support Clinical Decision Making," *JAMA*, vol. 258, No. 1, Abstract only, Jul. 3, 1987, Retrieved online from: Neonatology on the Web.
Sima, Chaoxin et al., "Vital Signs Services for Secure Telemedicine Applications" Proc AMIA Symp 1998: pp. 361-365.
Simon Project (Signal Interpretation and Monitoring), Vanderbilt University, Nashville, TN. Copyright © 2004 by Vanderbilt Universtiy, Retrieved from Internet: Page last modified Aug. 24, 2004, pp. 1-20.
Simpson, R. L., "Automating the ICU: Facing the Realities." *Nursing Management*, vol. 23, No. 3, Mar. 1992: 24-26.
Sipkoff, Martin, "Systems Aid Rural Health Delivery," Published by Premier Healthcare Resource Inc., Sep. 2003, pp. 1-4. Retrieved online from: QlPhysician.com.
Sittig, D. F. & M. Factor, "Physiologic Trend Detection and Artifact Rejection: A Parallel Implementation of a Multi-State Kalman Filtering Algorithm." In Symposium on Computer Applications in Medical Care, Nov. 5-8, 1989, Washington, DC; pp. 569-574.
Sittig, D. F. et al., "COMPAS: A Computerized Patient Advice System to Direct Ventilatory Care" Conference of Medical Informatics 88: Computers in Clinical Medicine, Institute of Measurement and Control for the British Medical Informatics Society, Nottingham, UK, Sep. 13 to 15, 1988; pp. 251-256.
Sittig, Dean F. et al., "Clinical Evaluation of Computer-Based Respiratory Care Algorithms" *International Journal of Clinical Monitoring and Computing*, vol. 7, 1990; pp. 177-185.
Sittig, Dean F. et al., "Computerized Management of Patient Care in a Complex, Controlled Clinical Trial in the Intensive Care Unit." *Computer Methods and Programs in Biomedicine*, vol. 30, 1989; pp. 77-84.
Sittig, Dean F. et al., "Computerized Screening for Identification of Adult Respiratory Distress Syndrome (ARDS) Patients" 1988 SCAMC, Inc., pp. 698-702.
Sittig, Dean F. et al., "Implementation of a Computerized Patient Advice System Using the HELP Clinical Information System" *Computers and Biomedical Research*, vol. 22, 1989; pp. 474-487.
Snowden, S. et al., "An Expert System to Assist Neonatal Intensive Care," *J Med Eng Technol*, vol. 21, No. 2, Abstract only, Mar./Apr. 1997, Retrieved online from: Neonatology on the Web.
Stewart. "Patenting of Software—Proposed Guidelines and the Magic Dividing Line that disappeared". JPTOS, pp. 681-698, Sep. 1995.
Stoodley, K. D. C. et al., "Problems in the Development of a Computerized Ward Monitoring System for a Pediatric Intensive Care Unit." *International J. Clinical Monitoring and Computing*, vol. 8, 1992: 281-287.
Sukavaara, T. et al., "A Knowledge-based Alarm System for Monitoring Cardiac Operated Patients—Technical Construction and Evaluation." *International J. Clinical Monitoring and Computing*, vol. 10, 1993: 117-126.
Szaflarski, N. L., "Emerging Technology in Critical Care: Continuous Intra-Arterial Blood Gas Monitoring." *American J. Critical Care*, vol. 5, No. 1, Jan. 1996: 55-65.
Tate, Karen E. and Reed M. Gardner, "Computers, Quality, and the Clinical Laboratory: A Look at Critical Value Reporting" Seventeenth Annual Symposium on Computer Applications in Medical Care, Oct. 30-Nov. 3, 1993, Washington D.C.; pp. 193-197.
Tate, Karen E. et al., "A Computerized Laboratory Alerting System" *M.D. Computing*, vol. 7, No. 5, 1990; pp. 296-301.
Tate, Karen E. et al., "Nurses, Pagers, and Patient-Specific Criteria: Three Keys to Improved Critical Value Reporting" 1995 AMIA, Inc.; pp. 164-168.

(56) References Cited

OTHER PUBLICATIONS

Thomas, Karl W. et al., "Evolution of Internet-Based Clinical Decision Support Systems," Journal of Medical Internet Research 1999; 1(2): e6 <URL: http//www.jmir.org/1999/2/e6/>, pp. 1-12.

Tobin, Martin, "Principles and Practice of Intensive Care Monitoring" McGraw-Hill, Inc., United States of America, 1998 (pp. 1-172 and pp. 1329-1407).

Tsien, Christine L. "Reducing False Alarms in the Intensive Care Unit: A Systematic Comparison of Four Algorithms" Proceedings Annual *AMIA* Fall Symposium (Paper on CD-ROM) 1997.

Tsien, Christine L. "Reducing False Alarms in the Intensive Care Unit: A Systematic Comparison of Four Algorithms" Proceedings Annual *AMIA* Fall Symposium (1997), p. 894.

Tsien, Christine L. and James C. Fackler "An Annotated Data Collection System to Support Intelligent Analysis of Intensive Care Unit Data." Proceedings of the Second International Symposium on Advances in Intelligent Data Analysis, Reasoning about Data; Aug. 4-6, 1997; X. Liu, P. R. Cohen, and M. R. Berthold, Eds.; Springer-Verlag, London, UK; pp. 111-121.

Tsien, Christine L. and James Fackler, "Poor Prognosis for Existing Monitors in the Intensive Care Unit" *Critical Care Medicine*, vol. 25, No. 4, 1997: 614-619.

Tsien, Christine L., "TrendFinder: Automated Detection of Alarmable Trends", Department of Electrical Engineering and Computer Science, Massachusetts Institute of Technology, Massachusetts; Jun. 2000.

Tsien, Christine L.. "Reducing False Alarms in the Intensive Care Unit: A Systematic Comparison of Four Algorithms" Proceedings *AMIA* Symposium, 1997. pp. 9-14 (unnumbered).

Uckun, S., "Intelligent Systems in Patient Monitoring and Therapy Management." *International J Clinical Monitoring and Computing*, vol. 11, 1994: 241-253.

Visicu/Cerner Complaint for Patent No. 6,804,656.

Wang, Kang et al., "A Real Time Patient Monitoring System on the World Wide Web," *Proceedings of the 1996 AMIA Annual Fall Symposium*, Abstract only, Hanley and Belfus, Inc., Nov. 1996, Retrieved online from: Neonatology on the Web.

Warner, Homer R. et al., "Computer-based Monitoring of Cardiovascular Functions in Postoperative Patients" *Supplement II to Circulation*, Vols. XXXVII and XXXVIII, Apr. 1968; pp. II-68 to II-74.

Webb, R. K., "Medical Decision Making and Decision Analysis." *Anesthesia and Intensive Care*, vol. 16, No. 1, Feb. 1988: 107-109.

Weil, Max H., "Use of Automated Techniques in the Management of the Critically Ill," *Hospital Information Systems*, Marcel Dekker, Inc., 1972, 333-381.

West Virginia University Research Corporation, Secure Collaboration Technology for Rural Clinical Telemedicine: Final Report, National Library of Medicine.

Westenkow, Dwayne R., "Automating Patient Care with Closed-Loop Control," *M.D. Computing*, vol. 3, No. 2, Abstract only, 1986, Retrieved online from: Neonatology on the Web.

Whiting, R and L. Hayes, "The Practice of Telemedicine—The TARDIS Perspective" *Informatics in Healthcare—Australia*, vol. 6, No. 3, Jul./Aug. 1997; pp. 103-106.

Yien, H. et al., "Spectral Analysis of Systemic Arterial Pressure and Heart Rate Signals as a Prognostic Tool for the Prediction of Patient Outcome in the Intensive Care Unit." *Critical Care Medicine*, vol. 25, No. 2, 1997: 258-266.

Young, W. Hsueh-fen et al., "Computerized Ventilator Data Selection: Artifact Rejection and Data Reduction," *International Journal of Clinical Monitoring and Computing*, vol. 14, May 5, 1997: 165-176.

Zhao, Ruilin, "A Model-Based Expert System for Interpretation of Hemodynamic Data from ICU Patients." Department of Electrical Engineering and Computer Science, Massachusetts Institute of Technology; May 18, 1997 (pp. 1-121).

Transaction History for U.S. Appl. No. 09/946,421, dated May 29, 2009.

Transaction History for U.S. Appl. No. 09/946,304, dated May 29, 2009.

Transaction History for U.S. Appl. No. 09/946,274, dated May 29, 2009.

Transaction History for U.S. Appl. No. 10/985,950, dated May 29, 2009.

Transaction History for U.S. Appl. No. 09/341,065, dated May 29, 2009.

Transaction History for U.S. Appl. No. 90/007,927, dated May 29, 2009.

Transaction History for U.S. Appl. No. 11/474,017, dated May 29, 2009.

Transaction History for U.S. Appl. No. 11/031,125, dated May 29, 2009.

Transaction History for U.S. Appl. No. 09/443,072, dated May 29, 2009.

Transaction History for U.S. Appl. No. 90/007,377, dated May 29, 2009.

Transaction History for U.S. Appl. No. 90/008,276, dated May 29, 2009.

Transaction History for U.S. Appl. No. 10/355,435, dated May 29, 2009.

International Searching Authority, Notification of Transmittal of the International Search Report and the Written Opinion of the International Searching Authority, or the Declaration for Application No. PCT/IB05/00646, dated Nov. 13, 2007, 9 pages.

Supplementary European Search Report for Application No. 05708735.5, dated Nov. 13, 2008, 4 pages.

Jury Verdict in *Cerner Corporation v. Visicu, Inc.*, Civil Action No. 04-1033 (W.D. Mo., Judge Gary A. Fenner), filed Dec. 8, 2009, 5 pages.

Non-final Office Action issued in U.S. Appl. No. 11/474,017, dated Mar. 31, 2010, 35 pages.

"Vital Signs," http://en.wikipedia.org/wiki/Vital-signs (accessed on Jun. 9, 2010), 5 pages.

Non-final Office Action issued in U.S. Appl. No. 10/985,950, dated May 14, 2010, 16 pages.

Non-final Office Action issued in U.S. Appl. No. 09/946,304, dated May 18, 2010, 15 pages.

International Search Report & Written Opinion in PCT application No. PCT/US10/25555, mailed Apr. 14, 2010, 7 pages.

Ouzzani, M. et al., "Ontological Approach for Information Discovery in Internet Databases." Distributed and Parallel Databases, 8, 2000, pp. 367-392.

Nenov, Valeriy et al., "Remote Analysis of Physiological Data from Neurosurgical ICU Patients," Application of Information Technology, Feb. 12, 1996, 3:318-327.

Bailes, Julian, "NeuroLink: A Neurosurgical Wide-Area Computer Network," Neurosurgery, vol. 35(4), Oct. 1994, pp. 732-736.

Pryor, Allan et al. HELP-a hospital-wide system for computer-based support of decision-making. Proceedings of the 14th Annual Hawaii International Conference on Systems Sciences; Jan. 8, 1981.

Visicu/Cerner Complaint for Patent No. 6,804,656, filed Nov. 12, 2004.

West Virginia University Research Corporation, Secure Collaboration Technology for Rural Clinical Telemedicine: Final Report, National Library of Medicine. Accessed online on Oct. 3, 2013, http://collab.nlm.nih.gov/tutorialspublicationsandmaterials/telesymposiumcd/WVafnl.pdf.

\* cited by examiner

MEDICAL INFORMATION QUERY SYSTEM

FIELD OF THE INVENTION

The inventive concepts relate to network computer systems and methods. More specifically, the present invention relates to systems and methods for creating, customizing and performing queries of medical data, such as patient, resource, or hospital data.

BACKGROUND

When an individual is admitted as a patient into a hospital, certain information about the patient must be acquired and made available to various members of the hospital staff. Such information includes, for example, the patient's identity, address, age and occupation, next of kin, medical history, conditions for which treatment is sought, preexisting conditions, and any medical insurance information.

During a patient's stay in a hospital, written information relating to his medical history, doctors' and nurses' observations and remarks, laboratory reports, diagnoses, doctors' orders, prescriptions and other notes by the medical team, including doctors, nurses, technicians, orderlies and the like, become part of the patient's file. Patients with chronic conditions or who are frequently hospitalized may have numerous files of substantial size which contain important historic, as well as current, information. The information that is necessary to provide a complete picture of the patient includes, for example, the patient's vital signs, fluid balance, respiratory function, blood parameters, electrocardiograms, x-rays, CT scans, MRI data, laboratory test results, diagnoses, prognoses, evaluations, admission and discharge notes, and patient registration information. This information originates from a variety of sources, including the patient, doctors, nurses, monitors connected to the patient, testing laboratories, the patient's medical records, and hospital administration records.

A massive amount of information about the patient is therefore generated in a relatively short time. Increasingly, this information is automatically recorded or manually entered into a computer-based medical information system. Critical care environments, such as hospital intensive care units, trauma units, emergency rooms and the like, are filled with state-of the-art electronic equipment for monitoring of patients. Such systems include a plurality of patient monitoring devices that record information related to the patient's status. These systems may also capture information about the medical resources being consumed.

Furthermore, many hospitals have changed the way in which patients are billed for services. In the past, patients were typically billed on the basis of days hospitalized. With recent changes in health care management and practice, patients are now more likely to be billed on the basis of treatments received. Greater efficiency in the treatment of patients is therefore emphasized. As a consequence, hospitals now scrutinize the effect of a treatment on a patient more closely, with increased monitoring, observation and recordation of the patient's responses to treatment. The burden of entry of the increased amount of information that must be recorded about a patient has been reduced by increased automation.

Commonly owned U.S. Pat. No. 6,322,502 B1 entitled Medical Information System provides an example of a system for obtaining data and information from and about patients in a hospital, and making it immediately and selectively accessible to various members of the medical team in a hospital in accordance with the functions performed by those members. This information may be displayed, at least in part, on screen in a flowsheet. To date, systems and methods for the automated robust query of such data and information are not provided, but could be extremely useful. For example, the ability to search across a plurality of patients with respect to a given set of parameters would provide a useful analytical tool for clinicians and administrators. Searches based on hospital or clinical resources would also help analyze and improve efficient distribution and usage of such resources.

SUMMARY OF THE INVENTION

In accordance with the present invention, a system and method are provided that enable the creation, customization, and performance of queries (or searches) of information collected, obtained, or stored in a medical information system. The results of such queries assist clinicians in their research, analysis, treatment, resource utilization, and quality assurance activities. A query wizard tool is provided for retrieving information from a medical information system, or its databases. Queries may be performed across a set of patients, hospitals or clinical resources. Query results are presented via an output device, such as a computer display. These results may be exported to other applications, such as known office or desktop applications, or other systems, such as database systems. Among other things, the query wizard tool facilitates creation of scripts for retrieval of information from the medical information system.

A typical medical information system in a clinic, hospital, or other medical facility may be a networked computer system that collects, stores, analyzes and manages a variety of types of data referred to as "patient data". Patient data may include dynamically changing data. Examples of dynamically changing patient data that may be monitored include a patient's heart rate, temperature, blood pressure, respiration rate, electrical brain activity, chemical balance or composition. Patient data may also include relatively static data, such as prior or current medical conditions, diagnosis, prognosis, statistics, and so on for one or more stays for each of a plurality of patients. These types of patient data are referred to as parameters, which may be grouped together as sets of related attributes. Many other types of patient data (or parameters) known in the art may also be collected or monitored. An account management system may be included as part of the medical information system, or it may be interfaced with the medical information system. The account management system typically stores patient account information, including patient name, address, telephone number, insurance information, billing and payment information, and the like, as static data.

Given the inclusion of dynamically changing patient data, monitors to collect in real-time or near real-time patient data during a patient's stay is also typically provided. Monitoring is typically accomplished, to some degree, using bedside units (BSUs), which are devices included in or configured to interface with the medical information system and posted proximate to the patient. BSUs may include output mechanisms such as display screens, printers, audible alarms, communication ports or some combination thereof, and input devices such as key pads, key boards, input ports, probes, sensors, cameras, recorders or interfaces to other data sources.

In accordance with the present invention, a query system is integral with or interfaced to the medical information system. The query system interfaces with the medical information system and various patient monitoring systems and devices.

The monitoring systems and devices make data available to the query system (via the medical information system) for retrieving data according to the query script. The query system may include or may be configured for access by any of a variety of devices, such as a desktop computer, workstation, laptop, personal digital assistant (PDA), telephone, server, or other network enabled device or programs, modules or components of such devices. That is, in accordance with various embodiments, query scripts may be defined, queries may be launched, or query results may be provided to or accessed by any of the above devices.

The query system includes a query wizard that provides a user interface for the creation, running and analysis of queries and query results. The query wizard includes logic and instructions necessary for establishing a graphical user interface for user devices (e.g., a desktop computer, workstation, PDA, and so on), generating and defining query scripts, processing inputs and outputs, and interfacing with other relevant devices and programs (e.g., operating systems, desktop applications, and so on). The query wizard may include program code distributed across various devices, e.g., arranged in a client-server architecture, or implemented in other manners known in the art. Preferably, the query wizard generates a user interface in a Web browser context and implements commonly available and known Web browser features, such as radio buttons, toolbars, drop-down lists, menus, text entry fields, graphical linking and so on.

Using the query wizard, queries are created by constructing a user (e.g., clinician or administrator) defined script that utilizes patient data. The algorithm embodied in the script is comprised of query attributes and related parameters, which form parameter-based tests or conditions to be met. As an example, a statement may be defined as "if temperature>100 degrees, then . . . ". Depending on the script, processing of patient data according to one or more statements returns certain results. The results may be provided on a display in a grid or table format, or they may be output in other forms, such as graphical plots or charts, audible speech or tones, dynamic video, of some combination thereof. Queries may be saved and attached to or embedded within other queries.

A set of filters may be defined and applied selectively to query attributes. For example, at least four types of filters may be applied to a given attribute: time, text, numeric, and checkbox. The time filter allows a user to apply specific time values to the selected query attribute(s). The text filter allows the user to include or exclude text values with or from the query. The numeric filter allows the user to include or exclude numeric values with or from the query and allows the application of statistical functions to filter data. The checkbox filter allows the user to apply "yes" or "no" values to query attributes.

BRIEF DESCRIPTION OF THE DRAWINGS

The drawing figures depict preferred embodiments by way of example, not by way of limitations. In the figures, like reference numerals refer to the same or similar elements.

FIG. 3A-3D are attribute filter screens rendered on a workstation by the query system of FIG. 1.

DETAILED DESCRIPTION OF THE PREFERRED EMBODIMENTS

A system and method in accordance with the present invention facilitate the creation, customization, and performance of queries (or searches) of information collected, obtained, or stored in a medical information system. The results of such queries assist clinicians in their research, analysis, treatment, resource utilization, and quality assurance activities. A query tool or wizard generates an interface for creating queries and retrieving information from a medical information system, or its databases. Through the query wizard a user can define a query by writing a script that indicates the types of attributes and parameters to be searched. Queries may be performed across a set of patients, hospitals or clinical resources. Query results are presented via an output device, such as a computer display. These results may be exported to other applications, such as known office or desktop applications, or other systems, such as database systems.

In the preferred form, a query system is used in conjunction with a medical information system, such as that described in U.S. Pat. No. 6,322,502B1. The medical information system may include or be used in conjunction with a clinical system that is used for administering clinical trials. In the preferred form, the medical information system includes bedside devices and systems (collectively "bedside units" (BSUs)) for patient monitoring and care. The medical information system provides a means for monitoring patients and collecting, storing, and maintaining patient data. Patient data may include a combination of relatively static and dynamically changing information related to a patient. Relatively static patient data may include the patient's name, address, and insurance information, as well information regarding the patient's medical history and prior care, diagnosis, prognosis, treatment and related information. Dynamically changing patient data may include a patient's heart rate, temperature, blood pressure, respiration rate, electrical brain activity, and chemical balance or composition.

Figure 1A:
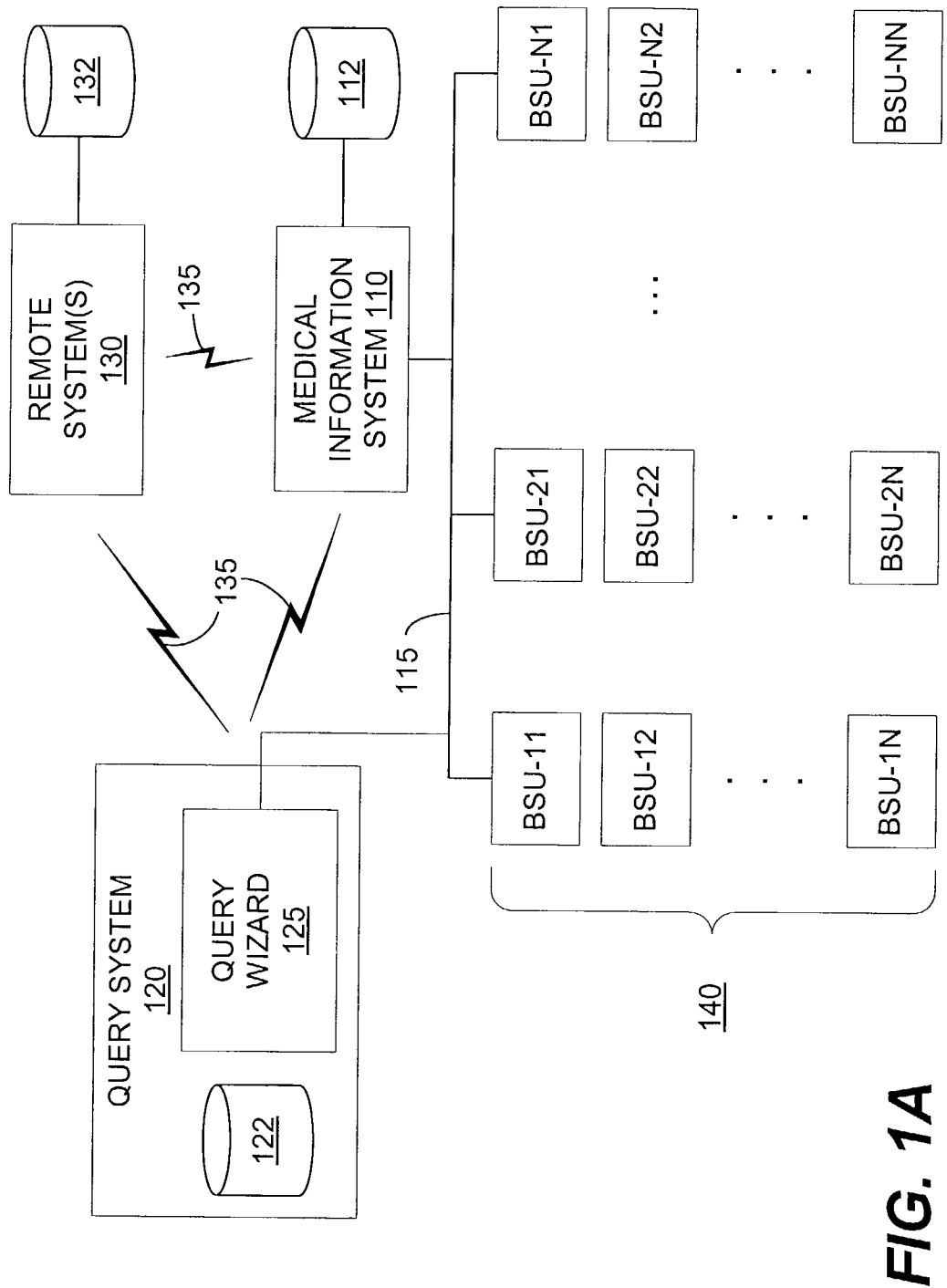
FIG. 1A is a diagram of a system architecture including a query system in accordance with the present invention.

The present invention may be implemented within the architecture depicted in FIG. 1A, as one possible embodiment. In this embodiment, a medical information system 110 comprises several workstations connected to a set of servers (not shown) via a network 115. The workstations and servers may be local, remote, or some combination thereof to each other. The medical information system 110 serves as the collector and maintainer of patient data, in a database system 112. The medical information system 110 includes a plurality of BSUs 140 that monitor patient status and collect patient data. In the preferred form, the BSUs also couple to network 115. Network 115 is depicted as a local area network (LAN) for simplicity. However, the present invention is not limited in this manner. Network 115 may by a LAN, wide area network (WAN), virtual private network (VPN), the Internet, World Wide Web or some combination thereof.

FIG. 1A shows a query system 120 in accordance with the present invention linked to medical information system 110 via network 115. There may additionally, or alternatively, be provided a wireless network link 135 between query system 120 and medical information system 110. The query system 120 may include its own database system 122 for storing information and data related to the queries (e.g., query scripts, algorithms, filter information and data) as well as results related data. In other embodiments, the query system 120 may be hosted on the same servers, workstations and computers as the medical information system 110 and may share at least a portion of database 112. Query system 120 and medical information system 110 may access, or may be accessed by, one or more remote systems 130, with their own database systems 132, for data access, exchange, or maintenance. For example, such remote systems 130 may include wired or wireless computers, servers, cellular telephones, pagers, personal digital assistants, e-mail devices, or other network, Web or Internet enabled systems or devices configured to create and launch queries and additionally, or alternatively, to receive query results. In the preferred embodiment, the query system 120 includes a query wizard 125 that facilitates the creation of query scripts using a scripting language, e.g., VB Script, although other programming languages may be used. In the preferred embodiment, a script is a VB Script function.

Figure 1B:
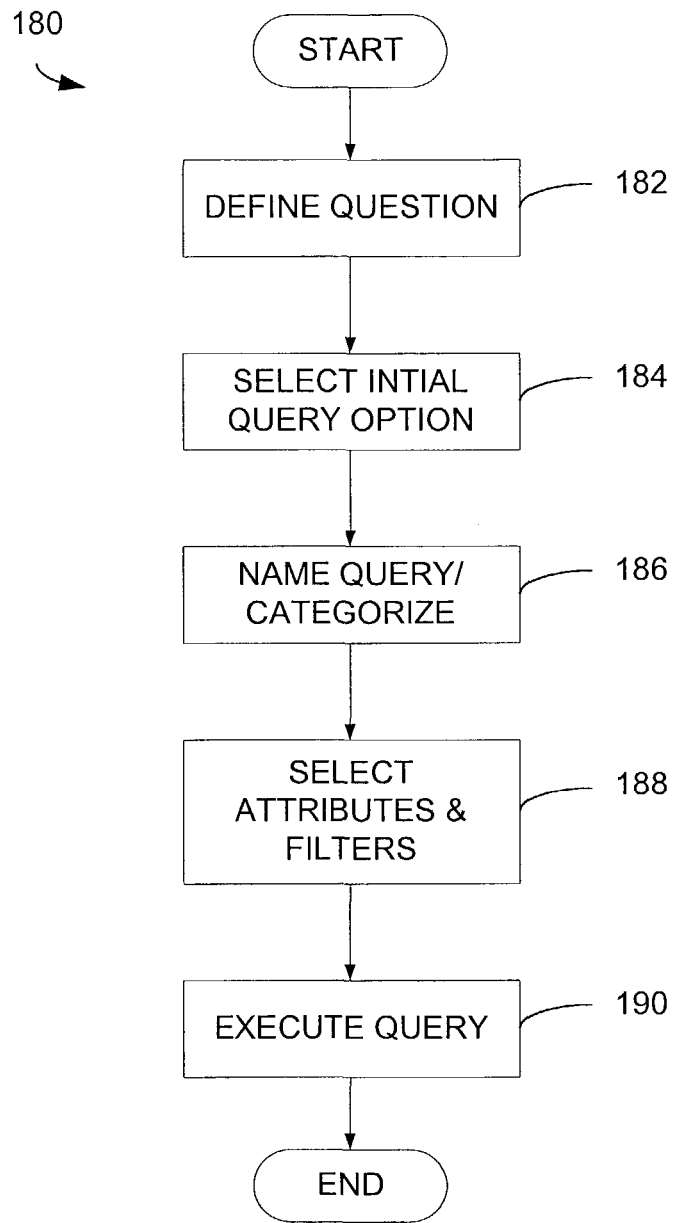
FIG. 1B is a flowchart depicting a query method in accordance with the present invention.

One embodiment of a query method in accordance with the present invention is depicted in the flowchart 180 of FIG. 1B. In this form, a user defines a question in step 182, selects initial query options in step 184, names and categorizes the query in step 186, selects the attributes and filters to be applied to the query in step 188, and may then execute the query in step 190.

Figures 2A, 2B:
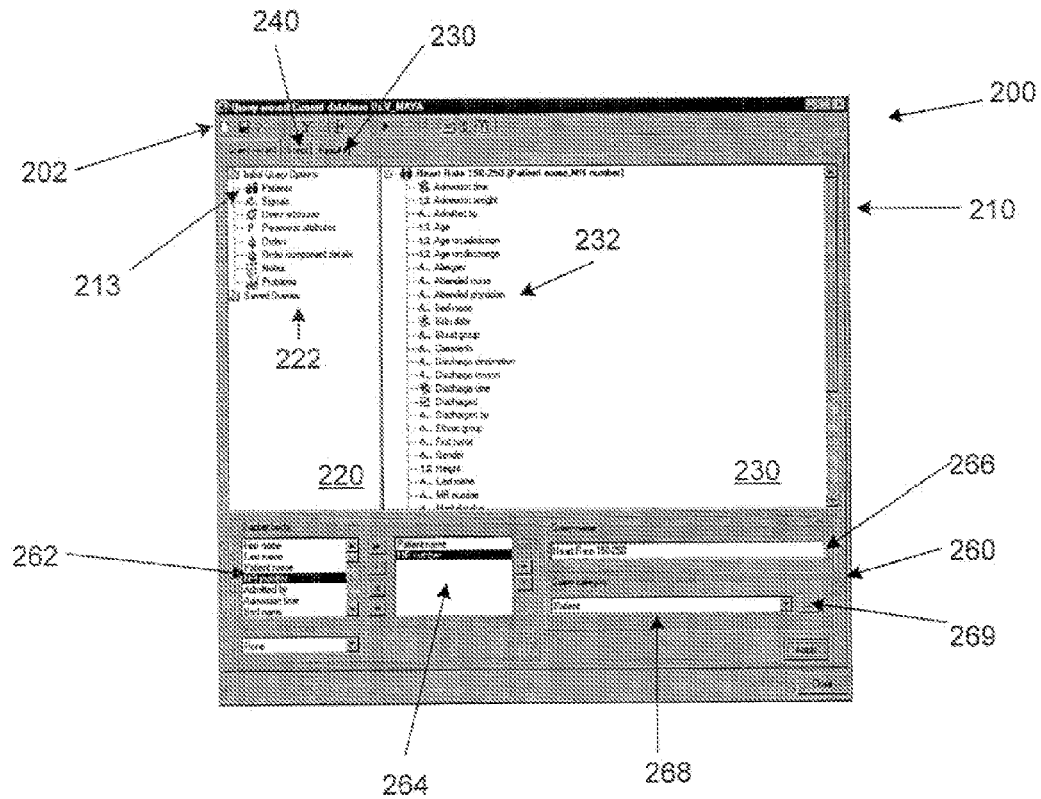
FIG. 2A-2D are query wizard screens rendered on a workstation of the query system of FIG. 1.

FIG. 2A illustrates an embodiment of a query wizard main screen 200 in accordance with the present invention. The query wizard main screen 200 facilitates the creation and launching of queries and presentation of query results. The query wizard main screen 200 comprises an icon toolbar 202, which contains icons for creating, saving, running, and sorting queries. The query wizard main screen 200 includes three tabs that facilitate creating queries and viewing results: Query Wizard, Script, and Results. These tabs reveal corresponding windows and panes having certain information and functionality associated therewith.

A New Query (NQ) icon is used to create a new query and a Save Query (SQ) icon saves the current query, i.e., the query that is open in the query wizard composition window 230. As part of the save function, the user is prompted to name the query. If the name typed already exists, the user will be prompted to type an alternative name. The query may be saved to the database chosen by user and is displayed in the Saved Queries folder of initial query options pane 220, which also includes a set of predefined attributes (e.g. Patients). A saved query can be retrieved from the database in which it was saved. A Saved Query Filter (SQF) icon allows a user to filter the display of saved queries.

A Delete Query (DQ) icon allows a user to delete its own query, but it is not possible to delete queries created by other users, in the preferred embodiment. An Attributes Filter (AF) icon causes the display or hiding of query attributes that were not used in the current query. A Change Database (CD) icon allows a user to select the database of another department from a list of databases. A database is usually named for the department to which it corresponds and is listed by department name in the query wizard 125. The database list includes online and archived offline databases, providing they are a part of a master list of accessible databases. Note that, in the preferred embodiment, changing databases selection may require authentication of the user, e.g., login via entry of a valid username and password, if access to that database is controlled.

An Export Query (EQ) icon allows a user to place its query results into another applications, e.g., a Microsoft Office™ application. (Note, Microsoft Office™, Word™, Excel™ and Access™ are trademarks of Microsoft Corporation, Redmond, Wash.). The Export Query icon is enabled only if there were results returned by the query. A Run Query (RQ) icon allows a user to run the query. A query may run for several minutes if the database is large and the requested information is distributed over numerous tables, query attributes, databases or systems. In one form, the query results are displayed in a grid in the Results pane 250 (see FIG. 2C). A Stop (S) icon is enabled during the processing of a query, e.g., while the results are being written to the Results pane 250.

Selection of a Sort by Query Category (SC) icon causes the display of saved queries by Query Category. Selection of a Sort by User Name (SN) icon causes the display of saved queries by name of the user that created them. An Open note (ON) icon appears in the toolbar 202 after a Notes query has been run. The Open note icon allows a user to open a note ('read-only') of a Notes query. An Export all notes (EN) icon also appears in the icon toolbar 202 after a Notes query has been run. This icon is selected to export all the notes of the Notes query results page to an editable Microsoft Word™ document.

A Query Filter (QF) icon facilitates display of a query setup pane 260. The query setup pane 260 comprises several selection mechanisms. For example, a Display Fields area 262 provides a list of fields for selection by the user. Selected display fields are entered into query fields area 264; these are the fields to be displayed in the Query Results pane 250 when the query is run. The user may also define a name for its query from Query Name area 266 and choose a category from Query Category 268. Setup pane 260 is discussed in greater detail below, with regard to building a query.

A Query Wizard window 210 is comprised of two panes, an initial query options pane 220 and the composition pane 230. An Initial Query Options tree 222 is included in the initial query options pane 220 and a query attributes tree 232 is included in the query attributes pane 230. Initial query options are selected and "dragged" from the Initial Query Options tree 222 to composition pane 230 to yield the query attributes tree 232. The setup pane 260 is also included in query wizard screen 210, and includes different user selectable filter options.

The initial query options pane 220 is a source to help define the type of query to be performed by dragging an option into the composition pane 230. For example, a Patients query type retrieves data from the medical information system 110 patient files and discharge forms, known in the art. A Signals query type retrieves data from the medical information system 110 flowsheet. A User Attributes query type retrieves data from the medical information system 110 user list. A Parameter Attributes query type retrieves data from a parameter properties form. An Orders query type retrieves data from an order list, with some additional data from an order entry form. An Order components details query type retrieves data on specific order parameters. A Notes query type retrieves data from the Notes module of the query wizard. A Problems query type retrieves data from a problem list, or database.

Selection of the Script tab causes presentation of a Script pane 240, shown in FIG. 2B. The Script pane 240 includes VB script that represents the query that was created from the Query Wizard window 210. The script in Script pane 240 may also be used as a part of a MS Word™ or Excel™ template that produces a table similar to the one displayed in Results pane 250, shown in FIG. 2C. Results pane 250 includes the results of the query created in the composition pane 230, after it is run. In this example, the results are displayed in a table that includes columns with details from the display fields selected for the query from setup pane 260.

Building a Query

At a top level, the procedure for building a query includes of the following steps: (1) defining a query (i.e., the "first" and "second" part of the user's question); (2) dragging and dropping the appropriate options from Initial Query Option tree 222 into the composition pane 230; (3) naming the query and choosing an appropriate Query Category in setup pane 260; (4) defining the display fields; and (5) defining the query attributes and setting the appropriate filters. After the query is built, the user may continue by: (6) running the query; and (7) saving the query and/or export the query results. This process is depicted in the flowchart 200 of FIG. 1B.

At a more detailed level, queries may be built step-by-step starting from the query wizard main screen 200 shown in FIG. 2A. A new query may be created according to the following steps:

Step 1: In this step, the user defines a query. The initial task in the query building process is the formulation of a query question. That is, the user must determine what it is that the user wants to know and exactly what type of results information is required. As an example (i.e., Example 1), suppose the user wants to know: "Which patients have had heart rate values between 150 and 250?" And, a definition of the required results information is "Display a list of patients that will include patient name and hospital number." Formulation of this query for query wizard 125 would be "Retrieve a list of patients (names+hospital numbers) with heart rate values greater than 149 and less than 251 with their Heart Rate values displayed."

Step 2: In the second step, the user selects the desired initial query options by dragging and dropping the appropriate options from the Initial Query Option tree 222 of FIG. 2A into the composition pane 230, both of query wizard window 210. The initial query option is selected to reflect the first part of the original question, which in Example 1 was "Which patients . . . ?". Once dropped into composition pane 230, a corresponding attributes tree 232 for the Patients query option is presented. For example, the attributes tree includes patient related attributes, such as Admission time, Admission weight, Admitted by. Therefore, continuing Example 1, since the user asked a question about "which patients", the Patients option 213 is selected and dragged into the composition pane 230.

Step 3: In the third step, the user names the query and chooses an appropriate query category. To accomplish this, the user enters a query name in the Query name field 266 of the setup pane 260. In the preferred form, by default, the name of the option selected from the Initial Query Options tree 222 is written into the Query name field 266, but can be overwritten by the user. Preferably, the user defined query name describes the contents of the query being created. Continuing with Example 1, assuming the category Patients has been selected, the user enters a user defined query name "HR 150-250" into Query name field 266.

To simplify the process of saving and finding queries, they must be saved in an existing query category. Referring to FIG. 2A, the user selects a query category from the Query category drop-down list 268. In the preferred form, the Query category drop-down list 268 may include a variety of categories, put the "Patient" category is shown as a representative category in FIG. 2A. Otherwise, the user can create a new category. To create a new category, the user can select the button 269 corresponding to the Query Category field 268; which causes a Customize Query Categories window to be presented. This window includes a text entry field for entering and saving a new category name.

Figures 2C, 2D:
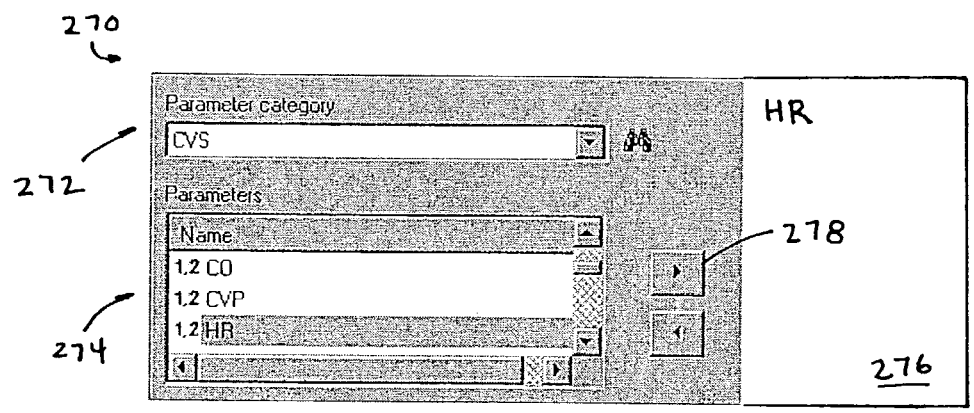

Step 4: In this step, the user selects the display fields for the query results. The display fields will dictate the determination and presentation of the query results. When the results are provided in a table or grid format, as is shown in FIG. 2C, the selected display fields become the names of the columns that will appear in the results table. Otherwise, the query results may be provided in other graphical, textual, audio or video forms, or some combination thereof.

Referring to FIG. 2A, the user can choose desired display fields from the Display field area 262 of the setup pane 260. To accomplish this, the user selects a desired display field (e.g., Patient name) and then selects the right arrow button (i.e., ">"), which causes the selected display field to be represented in the query fields area 264. In this manner, display fields may be selectively chosen, one-by-one. Otherwise, the user may select the double-arrow button (i.e., ">>") to have all the display fields represented in the query fields area 264, in one action. To deselect display fields the user can select the display field from query fields area 264 to be removed and click the appropriate return arrow buttons (i.e., "<" or "<<"). Once all desired display fields are represented in the query fields area 264, the user selects the Apply button of setup pane 260 to associate the selected display fields with the query name. The query name and the display fields are then represented in the composition pane 230. Continuing Example 1, the user defines the Patient Name and Hospital Number display fields. And, the query attributes tree has a heading comprising the query name and display fields, i.e., Hear Rate 150-250 (Patient name, MR number). "MR" indicates a specific medical facility.

Step 5: In this step, the user defines or selects the query attributes and sets the appropriate filters. This step relates to the second part of the original question (i.e., in Example 1: " . . . heart rate values between 150 and 250?"). The requested parameters or attributes (e.g., Heart Rate) are represented in the medical information system database 122. Selecting the query attributes is accomplished by first choosing the appropriate attribute from the query attributes tree 232. As mentioned above, query attributes tree 232 includes attributes that are related to the option (e.g., Patients) initially selected from the Initial Query Options tree 222, and includes the heading Heart Rate 150-250 (Patient name, MR number).

As also mentioned above, query attributes tree 232 includes, Sets of attributes not particularly related to the initially selected query option. The Sets, may be represented as expandable folders or trees of attributes that are, for the most part, not found in the portion of the query attributes tree 232 related to the selected initial query option. When a Set is selected, it expands to a query attributes tree (or sub-tree) comprised of attributes for the given Set. In the embodiment of FIG. 2A-2D, the attributes represented in the query attributes tree 232 are predefined and vary depending on the selected initial query option.

If the user's desired attributes, given the user's question, are attributes related to the query option selected from the Initial Query Options tree 222, then the user selects the desired attribute(s) from the query attributes tree 232 of the composition pane 230. If not already open, filter pane 270 is opened to facilitate the selection and definition of filters related to the selected attribute, as discussed below. The filter pane may be opened by selection of the Query Filter icon of toolbar 202.

If the desired attributes are related to an option not initially selected from the Initial Query Options tree 222, then the user selects the attribute Set that includes the desired attributes from the end of the query attribute list 232. Selecting the attribute Set reveals a new query attribute tree or subtree. In order to use the Display fields of the selected Set, the user selects the Set and proceeds in selecting and applying query results fields as described with respect to Step 4 above. That is, the contents and choices of the Display fields area 264 are context sensitive with respect to the chosen attribute Set in the composition pane 230. From the presented query attribute tree 232 the user selects a desired query attribute to be applied to the user's named query. Again, the user can open the filter pane 270 using the Query Filter icon.

In addition to use of the Query Filter icon, the query wizard can be configured to automatically render filter pane 270 upon selection of an attribute from composition window 230. Filter pane 270 is used to select attribute parameters and comprises a Parameter category drop-down list 272, a Parameters list 274, and a selected parameter area 276. Selection of a parameter category yields a list of related parameters in Parameters list 274. Those parameters in Parameters list 274 are eligible for selection into selected parameters area 276, and then for application to the query attribute. As is shown in FIG. 2D, a parameter category CVS is selected and a related parameter 1,2 HR is also selected.

Again, continuing Example 1, the user can chose and apply attributes and related parameter to have heart rate values returned by the query. To accomplish this, the user conducts the following steps:

1. Select the Signals Set query option from the query attribute list 232.
2. From the Display fields area 262 revealed for the Signals Set query option, select Value (not shown).
3. Select the Heart Rate attribute from query attribute tree 232.
4. In the filter pane 270, select the parameter category from the Parameter Category drop-down list 272 that contains the Heart Rate is a parameter.
5. Select the HR parameter from the scrollable Parameters list 274.
6. Select the right arrow button 278 (i.e., ">") to move the highlighted parameter to the selected parameter area 276.
7. Click Apply button.

Figures 3A, 3B, 3C:
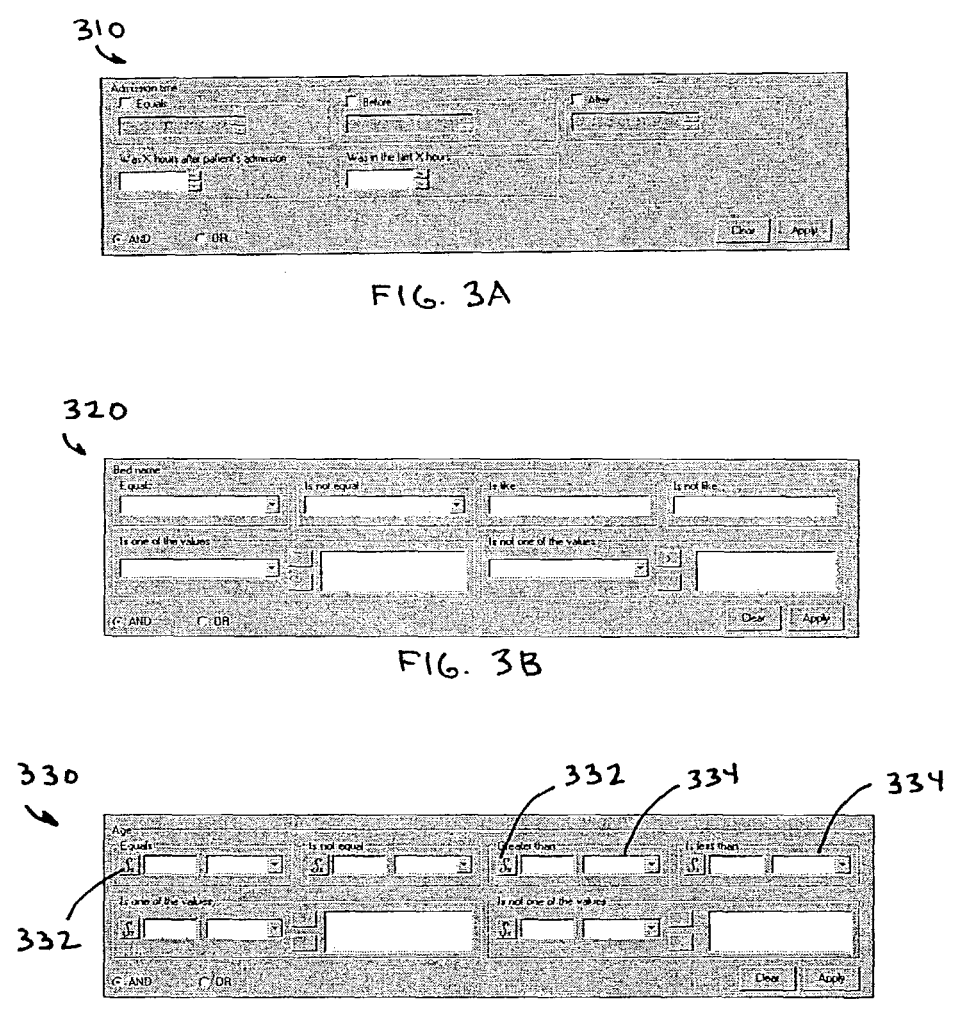
Figure 3D:
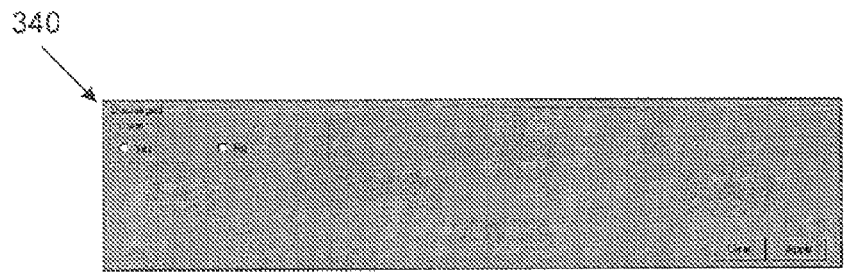

As discussed above, for each selected attribute, filters can be defined and applied. Filter types vary depending on the query attribute chosen. In the preferred embodiment there are four filter types available: time, text, numeric, and checkbox. A different filter form is revealed for each filter type, providing mechanisms that allow the user to define and apply the filter. The time filter type allows a user to apply relative time values to its query (for example, before or after), as is shown in the time filter pane 310 of FIG. 3A. The text filter type allows a user to include or exclude text values with or from its queries (for example, equals or is like), as is shown in text filter pane 320 of FIG. 3B. The numeric filter type allows a user to include or exclude relative numeric values to its queries (for example, equals to, greater than or less than), as is shown in the numeric filter pane of FIG. 3C. As discussed in greater detail below, statistical functions can be applied to numeric type filters using the statistical functions buttons 332. The checkbox filter allows a user to apply Yes or No values to query attributes, as is shown in checkbox filter pane 340 of FIG. 3D.

A user may combine several filter options by using the And or Or selection which appear within the filter pane 270. Additionally, other filters may be defined for specific attributes, such as a Problem Number filter type for the Problems initial query option. To set a filter, the user completes the filter forms of FIGS. 3A, 3B, 3C, and/or 3D and then selects the Apply button. These steps are repeated for every additional query attribute that the user wishes to filter for its query. To clear a set filter the user selects the attribute item from the query attribute tree 232, which reveals the filter forms 310, 320, 330, and 340. The user then selects the Clear button in the appropriate filter form. To view only the attributes being used in the query, click the query Attributes Filter icon from the toolbar 202.

Continuing with Example 1, to filter heart rate values, click the Value query attribute (not shown) under the Heart Rate 150-250 (Patient name, MR number) of query attributes tree 232. The numeric filter 330 of FIG. 3C is set as follows: (1) In the Greater than field, enter 149 and choose Beats Per Minute from the units drop-down list 334; (2) In the Is less than field, enter 251 and choose Beats Per Minute from the drop-down list; (3) Select the AND option; and (4) Click Apply, a numeric filter indicator (e.g., 1,2) appears in bold text next to the selected query attribute in the composition window 230 (see FIG. 2A for examples). The query is now fully defined and can be run by selecting the Run Query icon.

As another example (i.e., an Example 2) a user may ask the questions "Which patients have received Dopamine at a dosage of less than 3 Mg/Kg/Min and when?" This query may be defined as follows: (1) Select the Patients option from Initial Query Options list 222 and drag it to the composition window 230; (2) Enter a name for the query in the Query name field of setup pane 260; (3) Select the Query category from the drop-down list 268; (4) Select the following display fields for the query: Patient Name and MR number; (5) Click Apply; (6) Select the attribute Set containing Orders information from the end of the query attributes tree 232 of composition window 230; (7) Select the following display fields for the Orders Set: Rate, Start time, End time, and Planned time; (8) Select the appropriate query attribute(s): To query the database for this specific dosage of Dopamine, select the Main substance query attribute from the query attribute tree 232; (9) The Order Parameter category field 272 (see FIG. 2D) then shows all the main substance categories; (10) Select the Orders Parameter category that contains Dopamine; (11) Select Dopamine from the Orders Parameters list 274 and click the right arrow to move it to the Selected orders parameters list 278; and (12) Click Apply. In response, the Dopamine attributes appear in the Main substance tree 232.

To filter the Dopamine rate values: (1) Select the Rate attribute from Main substance tree 232; (2) To set the filter choose the Query Filter icon from icon toolbar 202, which reveals the filter panes of FIGS. 3A, 3B. 3C, and 3D; (3) Enter 3 in the Is less than field of the numeric filter pane 330 and choose Mg/Kg/Min from the drop-down list; and (4) Click Apply. In response, the filter icon appears in bold text next to the selected query attribute.

Order parameters in the query system 120 depend upon the customization of the database being queried, e.g., medical information system database 122. For example, a user can query Albumin as an ingredient as well as a main substance or a mixed solution. Should the user have any problems locating the substance to be queried, a search for the substance in a medical information order entry form (known in the art), or database, can be conducted using the query wizard 125.

Once defined, as discussed above, a query can be run by actuating the Run Query icon of icon toolbar 202 (see FIG. 2A). Results are viewed in Results pane 240.

Queries can also be saved by selecting the Save Query icon of icon toolbar 202. Once saved, the query is available in the Saved Queries folder of the Initial Query Options tree 222. The user can filter the display of the saved queries by clicking the Saved Query Filter display options in the icon toolbar 202.

By filtering the display of saved queries, it is meant that a subset of the saved queries can be culled from the full set of saved queries.

Figure 4:
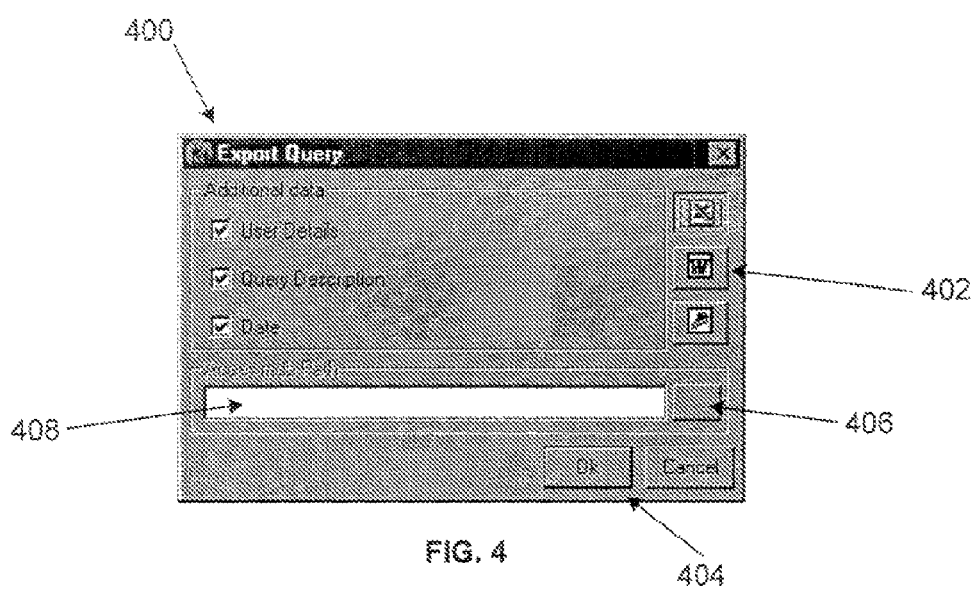
FIG. 4 is an exemplary export query screen rendered on a workstation by the query system of FIG. 1.

As previously mentioned, query results can be exported to other applications, e.g., to a Microsoft Word™ or Excel™ file or to a Microsoft Access™ database. The results may then be further processed, if desired. To export query results:

1. Select the Export Query icon to open the Export Query dialog box 400 of FIG. 4.

2. Choose one of the three Microsoft Office™ applications from the application icon buttons 402 of dialog box 400.

a) To export to Word™ or Excel™, select the appropriate Word™ or Excel™ icon from dialog box 400 and then select the Ok button 404. The query results appear in the appropriately formatted document.

b) To export to Access™, select the Access™ icon. Then, select the browse (or " . . . ") button 406. Browse to and select one existing Access™ databases (i.e., files with a "mdb" extension). Otherwise, type the name of an existing or new table for storing the results in text entry field 408 and then select the Ok button 404. After exporting the query, it may be printed from the application to which it was exported.

Using the query wizard 125, a user can build complex queries by combining multiple queries. To accomplish this, the user can add one or more saved queries to a query under composition in the composition window 230 of FIG. 2A. For instance, the user can:

1. Select the New Query icon from icon toolbar 202.

2. Drag an option from the Initial Query Options tree 222 to the composition window 230.

3. Define and name the new query, as previously described.

4. Drag a saved query from the Initial Query Options tree 222 over the Sets (not shown) in the composition window 230; the compatible Sets will be highlighted.

5. Drop the saved query in one of the compatible Sets.

The user is then presented with the option of attaching or embedding the saved query to or in the new query. Attaching the query creates a link between the saved query and the new query. Any changes that are made to the saved query will directly influence the new query. Embedding the query adds a copy of the saved query to the new query. Whenever changes to an attached query are made, the query will automatically be updated. Changes made to an embedded query will not affect the previously saved version of the embedded query.

In accordance with the present invention, beyond the functions that enable the creation, running, and saving queries, statistics functions may also be included. Preferably, the query wizard 125 includes an option for using three levels of statistical functions. The first level enables a user to perform statistical functions or calculations upon the query results. The second level enables a user to apply statistical filters as a part of the query. The statistical calculations apply to all values. And, the third level lets a user define the group of values or the sample of patients on which the user wants to perform the statistical calculations.

Figure 5A:
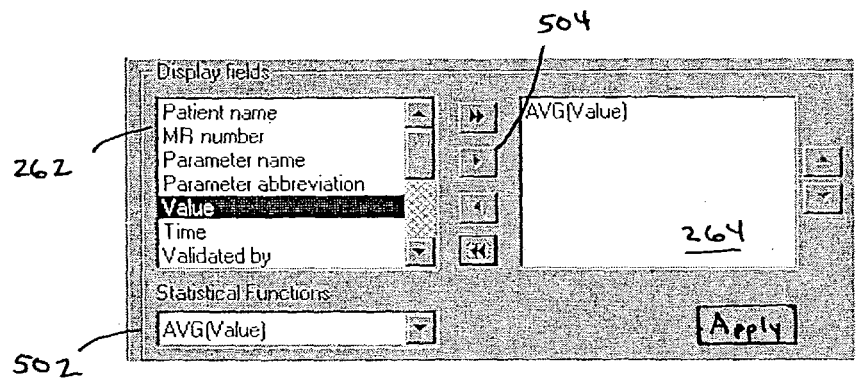
FIG. 5A-5B are exemplary screen shots related to use of statistical functions and rendered on a workstation by the query system of FIG. 1.

Statistical Functions. A display statistical functions utility allows a user to make statistical calculations based on the results of the query (such as average Heart Rate (HR) for a specific patient). This function may also be used to display the results of a statistical function applied to all values (for example, the average HR for all patients). In the case of our Example 1, for patients with HR between 150-250, the display statistical functions utility enables one to add the average age of these patients to the display fields, for example. To display statistical functions:

1. Choose the Display fields 262 (see FIG. 5A) intended for use with the statistical calculation.

2. Select a function from the Statistical Functions drop-down list 502 associated with the Display fields list 262.

3. Select the central arrow 504 to move the display field to the window display fields pane 264.

4. Select Apply.

Other typical statistical functions known in the art may also be defined and included.

Statistical Filters. The numeric filter pane 330 of FIG. 3C includes statistical functions, which a user can choose from the drop-down list of the statistics button 334 beside each field of a filter. This filtering function enables the user to view values above or below the average, min/max values, and so forth. The user can, for example, use this statistical filter to display all patients who have had HR above average by using the statistical functions key 334, in FIG. 3C. In the preferred form, the Statistical Function filters (e.g., average value) are calculated from the entire database upon which the user is working. However, the display statistical function is calculated only for the results of the query.

To apply statistical function filters: (1) select the statistics button 332 beside the desired field (e.g., Greater than, Less than, etc.) in the numeric filter pane 330; (2) choose the required statistical function filter from the drop-down list presented; the statistical function filter appears in the field besides the statistics button 332 and the units field 334 disappears; and (3) select the Apply button.

Figure 5B:
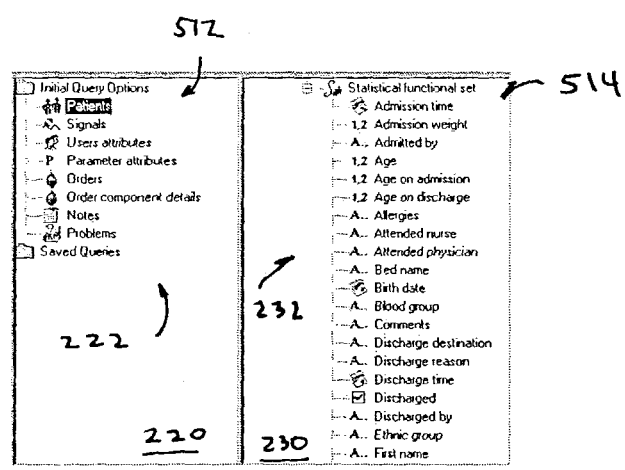

Statistical Function Set. The Statistical function set allows a user to perform statistical calculations only on selected groups of values, such as values without error or validated values. Any filter applied to this set defines the sample on which the statistical calculations are performed. Referring to FIG. 5B, in the Patients 512 initial query option, every definition in the Statistical function set 514 determines the relevant sample of patients. For instance, defining Age>60 as a Statistical function set will determine which patients are used for the query Height>AVG(Height). The average will be the average height of patients over 60 years old.

Setting a Statistical function set is done as any other set: (1) Select the Statistical function set. An additional query attribute tree opens, as part of the existing query attributes tree, containing the same attributes as the initial query option being worked on; (2) Select the desired query attribute from the new query attributes tree; (3) Set the required filters, as previously discussed; and (4) Select the Apply button.

If the user builds a query that looks for HR>AVG (HR) in the statistical function filter, and define HR>100 in the Statistical function set, the average HR in this query will be calculated only from those HR signals that are greater than 100. However, if the user defines the Statistical function set as HR>100, and then build a query that looks for HR>90 and HR<110, the user will still see values under 100, since the Statistical function set only defines the sample for statistical functions, not for all types of queries. In addition, when the user defines the Statistical function set for a specific parameter, it will only affect the statistical calculations of that parameter. Thus, defining HR>100 as a Statistical function set will have no affect on the query BP>AVG(BP).

Time-Related Parameters. The time-related parameters function allows querying of signals and orders that have a relationship in time, e.g., within the same time frame. The time-related attribute defines the point or period in time on which the whole query is based.

As an Example 3, to find the Blood Pressure values at around the time the Heart Rate was over 150:

1. Under Parameters set (not shown), which is located with the other Sets found at the end of the query attributes tree, choose Parameters.

2. In the filter pane 270, select the Parameter category that contains the Blood Pressure parameter.

3. Select the Blood Pressure parameter.

4. Under Time related parameters, choose Parameters.

5. In the filter pane 270, select the Parameter category that contains the Heart Rate parameter.

6. Select the Heart Rate parameter. The HR value appears in the composition window 230.

7. Highlight the Value query attribute from Display field 262 (see FIG. 5). A numeric filter pane 330 is rendered in the filter pane 270.

8. Define HR>150 in the numeric filter pane 330.

Figure 6:
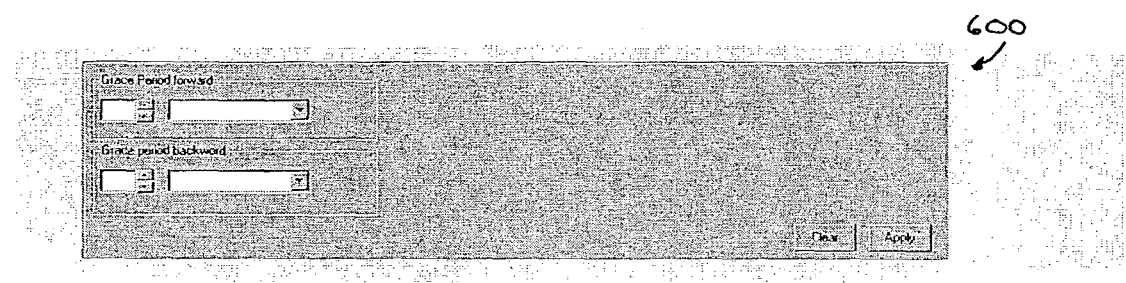
FIG. 6 is an exemplary screen shot of a grace period entry form rendered on a workstation by the query system of FIG. 1.

9. Highlight the Grace period query attribute. A grace period filter 600 of FIG. 6 appears in filter pane 270.

10. Enter a grace period of 5 minutes forward and backwards.

This query will look for blood pressure values from 5 minute before and after each value of HR greater then 150.

As an Example 4, to find out how much Potassium was given during the hour following a lab result of $K^+$<3.5. Define parameter $K^+$ under the Time related attribute as $K^+$<3.5, with a grace period of 1 hour forward. The query will look for the amount of potassium given during the hour following that lab result.

While the foregoing has described what are considered to be the best mode and/or other preferred embodiments, it is understood that various modifications may be made therein and that the invention or inventions may be implemented in various forms and embodiments, and that they may be applied in numerous applications, only some of which have been described herein. As used herein, the terms "includes" and "including" mean without limitation. It is intended by the following claims to claim any and all modifications and variations that fall within the true scope of the inventive concepts.

What is claimed is:

1. A query system, configured to access or obtain patient data from a medical information system comprising a set of electronic patient monitoring devices, wherein said query system comprises:
  A. a query script generator configured to apply an executable scripting language to a set of query attributes associated with elements of a subset of data of multiple patients, the query script generator defining and storing one or more query scripts as representations of at least some of the query attributes in the applied executable scripting language, wherein the one or more query scripts include a selectable statistical filter that narrows the subset of data of multiple patients based on an application of a statistical function on a group of values selected from a second subset of data of multiple patients;
  B. a query script executor, configured to apply said one or more query scripts to said data of multiple patients and to generate query results comprising said elements of said subset of data of multiple patients;
  C. an output generator, configured to output said query results; and
  D. a filter manager, configured to facilitate customization of the selectable statistical filter, the filter having a selectable value, and to apply said selectable filter and selectable value to said set of query attributes, wherein said selectable statistical filter is configured to narrow the subset of data of multiple patients.

2. The system of claim 1, wherein said query system includes a query wizard graphical user interface hosted on a query system electronic device and configured to facilitate user interaction with one or more of said query script generator, said query script executor, and said output generator.

3. The system of claim 2, wherein said query wizard graphical user interface is configured to render said query results.

4. The system of claim 2, wherein said query wizard graphical user interface includes an attributes pane comprising predefined user selectable attributes and a composition pane configured to accept selected attributes from said attributes pane to form said set of query attributes.

5. The system of claim 4, wherein said attributes pane and said composition pane are configured to facilitate dragging said selected attributes from said attributes pane and dropping said selected attributes into said composition pane.

6. The system of claim 4, wherein said query generator is configured to generate said one or more scripts in response said dropping said selected attributes into said composition pane and said query wizard further includes a script pane configured to render said one or more query scripts.

7. The system of claim 1, wherein said query system is hosted, at least in part, on said medical information system comprising the set of electronic devices.

8. The system of claim 1, wherein said query system couples to said medical information system via a LAN, WAN, virtual network, private network, the world wide web, the Internet, a telephone network, or some combination thereof.

9. The system of claim 1, wherein said query system includes a predefined set of initial query options each representing a different query category, wherein each initial query option is comprised of a set of selectable initial query option attributes, and wherein each initial query option is selectable as a template for generating said one or more query scripts.

10. The system of claim 1, wherein said selectable statistical filter is customized as a function of at least one of:
  a) time values;
  b) text values;
  c) numeric values; and
  d) yes or no values.

11. The system of claim 1, wherein said query system is further configured to define and apply the selectable statistical filter to said data of multiple patients.

12. The system of claim 1, wherein said query system is further configured to define and apply the statistical function to said query results.

13. The system of claim 1, wherein said query system is further configured to define and apply statistical function sets to selected groups of multiple patient data values of one of said set of query attributes.

14. The system of claim 1, wherein said query script generator is further configured to embed within or attach to said one or more query scripts a second query script.

15. The system of claim 1, wherein said output generator exports query results to an application file or database.

16. The system of claim 1, wherein said data of multiple patients includes data that is dynamically changing.

17. A method of querying patient data from a medical information system comprising a set of electronic patient monitoring devices, wherein said method of querying comprises:
  A. generating one or more query scripts by defining and storing the query scripts as representations of query attributes in an executable scripting language, including for each of said one or more query scripts applying the executable scripting language to a set of query attributes associated with elements of a subset of data of multiple patients, wherein one or more selectable statistical filters, each filter having a selectable value, configured to narrow the subset of data of multiple patients, are applied to said query attributes, wherein said one or more selectable statistical filters are included in said one or more query scripts and configured to narrow the subset of data of multiple patients based on an application of a statistical function on a group of values selected from a second subset of data of multiple patients;

B. applying said one or more query scripts to said data of multiple patients and to generate query results comprising said elements of said subset of data of multiple patients; and C. generating an output of said query results.

18. The method of claim 17, wherein said method includes generating a query wizard graphical user interface hosted on an electronic device, and wherein said query wizard includes graphical devices for performing steps A and B.

19. The method of claim 18, wherein said method further includes rendering said query results via said query wizard.

20. The method of claim 18, wherein said query wizard graphical user interface includes an attributes pane comprising predefined user selectable attributes and a composition pane, and wherein said step A includes selecting and dragging selected attributes from said attributes pane and dropping said selected attributes into said composition pane to form said set of query attributes.

21. The method of claim 20, wherein said wizard graphical user interface includes a script pane, and step A further includes generating said one or more query scripts in said script pane in response to said dropping said selected attributes into said composition pane.

22. The method of claim 18, wherein said method of querying is carried out, at least in part, on said medical information system set of electronic devices.

23. The method of claim 18, wherein one or more of steps A, B, and C are carried out by a wireless device.

24. The method of claim 18, wherein said method includes coupling to said medical information system via a LAN, WAN, virtual network, private network, the world wide web, the Internet, a telephone network, or some combination thereof.

25. The method of claim 18, wherein said method includes providing a predefined set of initial query options each representing a different query category, wherein each initial query option is comprised of a set of selectable initial query option attributes, and step A includes:

1) selecting one of said initial query options as a template for generating said one or more query scripts.

26. The method of claim 17, including customizing said one or more selectable statistical filters as a function of at least one of:

a) time values;
b) text values;
c) numeric values; and
d) yes or no values.

27. The method of claim 18, further including defining and applying the one or more selectable statistical filters to said data of multiple patients.

28. The method of claim 18, further including defining and applying the statistical function to said query results.

29. The method of claim 18, further including defining and applying statistical function sets to selected groups of the multiple patient data values of one of said set of query attributes.

30. The method of claim 18, further including embedding or attaching to said one or more query scripts a second query script.

31. The method of claim 18, further including exporting query results to an application file or database.

32. The method of claim 18, wherein said data of multiple patients include dynamically changing multiple patient data.

* * * * *